(12) United States Patent
Hilpert et al.

(10) Patent No.: US 11,447,478 B2
(45) Date of Patent: Sep. 20, 2022

(54) BACE1 INHIBITORS

(71) Applicants: Hoffmann-La Roche Inc., Nutley, NJ (US); Siena Biotech S.p.A., Siena (IT)

(72) Inventors: Hans Hilpert, Muenchenstein (CH); Roland Humm, Auggen (DE); Thorsten Muser, Loerrach (DE); Christian Schnider, Basel (CH); Roger Wermuth, Sissach (CH); Thomas Woltering, Freiburg (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 518 days.

(21) Appl. No.: 14/783,478

(22) PCT Filed: Apr. 8, 2014

(86) PCT No.: PCT/EP2014/056985
§ 371 (c)(1),
(2) Date: Oct. 9, 2015

(87) PCT Pub. No.: WO2014/166906
PCT Pub. Date: Oct. 16, 2014

(65) Prior Publication Data
US 2016/0052920 A1    Feb. 25, 2016

(30) Foreign Application Priority Data

Apr. 11, 2013 (EP) .................................. 13163430

(51) Int. Cl.
    *C07D 413/14* (2006.01)
(52) U.S. Cl.
    CPC .................................. *C07D 413/14* (2013.01)
(58) Field of Classification Search
    CPC ......... C07D 413/14; A61P 25/00; A61P 25/28
    USPC ............................ 514/228.8, 277, 459, 476
    See application file for complete search history.

(56) References Cited

U.S. PATENT DOCUMENTS

| 8,999,980 | B2 | 4/2015 | Masui et al. |
| 2014/0051691 | A1 * | 2/2014 | Masui .................. C07D 413/12 514/228.8 |

FOREIGN PATENT DOCUMENTS

| WO | 2004058767 A1 | 7/2004 |
| WO | 2008141239 A1 | 11/2008 |
| WO | 2010098488 A1 | 9/2010 |
| WO | 2011069934 A1 | 6/2011 |
| WO | 2012139993 A1 | 10/2012 |
| WO | 2012156284 A1 | 11/2012 |
| WO | WO 2012/147763 A1 * | 11/2012 ........... C07D 413/12 |
| WO | 2012/168164 A1 | 12/2012 |
| WO | 2012168175 A1 | 12/2012 |
| WO | 2013027188 A1 | 2/2013 |
| WO | 2013110622 A1 | 8/2013 |
| WO | 2014065434 A1 | 5/2014 |
| WO | 2014134341 A1 | 9/2014 |

OTHER PUBLICATIONS

The European Communication, dated Nov. 11, 2016, in the corresponding European Patent Application No. 14715908.1.
The English translation of the Japanese Office Action, dated Dec. 12, 2017, in the related Japanese Appl. No. 2016-506890.
The International Search Report and Written Opinion, dated May 9, 2014, in the related PCT Appl. No. PCT/EP14/56985.
The Canadian Office Action, dated Apr. 27, 2020, in the related Canadian Appl. No. 2,900,433.
The English translation of the Japanese Office Action, dated Jul. 23, 2019, in the related Japanese Appl. No. 2018-194983.

* cited by examiner

*Primary Examiner* — Pancham Bakshi

(57) ABSTRACT

The present invention provides a compound of formula I having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

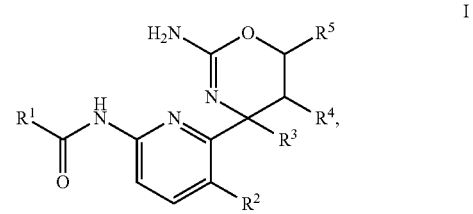

24 Claims, No Drawings

BACE1 INHIBITORS

CROSS-REFERENCE TO RELATED APPLICATIONS

This application is a National Stage Application of PCT/EP2014/056985 filed Apr. 8, 2014, which claims priority from European Patent Application No. 13163430.5, filed on Apr. 11, 2013. The priority of both said PCT and European Patent Application are claimed. Each of prior mentioned applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the transmembrane domain (TM) to produce a C-terminal fragment of APP containing the TM- and the cytoplasmic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36): 26326). It is thus presumed that inhibitors of BACE1 activity can be useful agents for therapeutic intervention in Alzheimer's disease (AD).

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 can in addition be used to treat the following diseases: IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 Jan. 29; 105(4):1291-6), Dermatomyositis (Greenberg S. A. et al., Ann Neurol. 2005 May; 57(5):664-78 and Greenberg S. A. et al., *Neurol* 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol Genet. 2006 Mar. 15; 15(6):965-77. Epub 2006 Feb. 8), Multiple Mieloma (Kihara Y. et al, Proc Natl Acad Sci USA. 2009 Dec. 22; 106(51): 21807-12), Malignant melanoma (Talantov D. et al, Clin Cancer Res. 2005 Oct. 15; 11(20):7234-42), Sjogren syndrome (Basset C. et al., Scand J Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

WO2013027188 describe 2-Amino-4-(pyridin-2-yl)-5,6-dihydro-4H-1,3-oxazine derivatives and their use as BACE-1 and/or BACE-2 inhibitors, EP2511268 and WO012147763 describe oxazine derivatives as BACE1 inhibitors.

The present invention provides novel compounds of formula I, their manufacture, medicaments based on a compound in accordance with the invention and their production as well as the use of compounds of formula I in the control or prevention of illnesses such as Alzheimer's disease. Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

FIELD OF THE INVENTION

The present invention provides Fluoromethyl-5,6-dihydro-4H-[1,3]oxazin-2-ylamines having BACE1 inhibitory properties, their manufacture, pharmaceutical compositions containing them and their use as therapeutically active substances.

SUMMARY OF THE INVENTION

The present invention provides a compound of formula I,

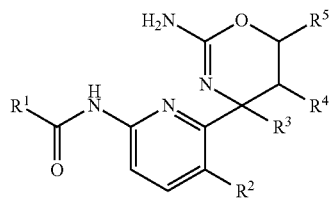

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Particular "$C_{1-6}$-alkyl" are "$C_{1-3}$-alkyl". Specific groups are methyl and ethyl. Most specific is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. Specific groups are difluoromethyl and trifluoromethyl.

The term "cyano-$C_{1-6}$-alkyl", alone or in combination with other groups, refers to $C_{1-6}$-alkyl as defined herein, which is substituted by one or multiple cyano, particularly 1 cyano. Examples are cyanomethyl, cyanoethyl and the like.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy, as defined herein, particularly 1 $C_{1-6}$-alkoxy. Particular "$C_{1-6}$-alkoxy-$C_{1-6}$-alkyl" is methoxy-$C_{1-6}$-alkyl. Examples are methoxymethyl, methoxyethyl and the like.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" is Cl and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl, pyrazinyl and 1H-pyrazolyl, as well as oxazolyl and 1H-pyrazolyl. Specific "heteroaryl" are pyridin-2-yl, pyrazin-2-yl and 1H-pyrazol-3-yl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific is methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy. Specific "halogen-$C_{1-6}$-alkoxy" is trifluoromethoxy.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular 1 $C_{2-6}$-alkynyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of $C_{2-6}$-alkynyl include ethynyl, propynyl, and n-butynyl.

The term "aryl" denotes a monovalent aromatic carbocyclic mono- or bicyclic ring system comprising 6 to 10 carbon ring atoms. Examples of aryl moieties include phenyl and naphthyl. Specific "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log Ki$), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino protecting group" (here also X) denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

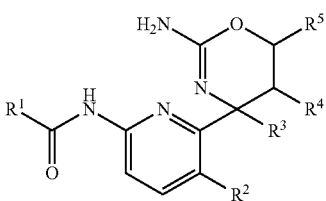

I wherein
$R^1$ is selected from the group consisting of
  i) aryl,
  ii) aryl substituted by 1-4 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
  i) hydrogen,
  ii) $C_{1-6}$-alkyl, and
  iii) halogen;

$R^3$ is selected from the group consisting of
  i) $C_{1-6}$-alkyl, and
  ii) halogen-$C_{16}$-alkyl, $R^4$ is selected from the group consisting of
  i) halogen, and
  ii) hydrogen, $R^5$ is halogen-$C_{1-6}$-alkyl;

or pharmaceutically acceptable salts thereof.

A certain embodiment of the invention provides a compound of formula Ia,

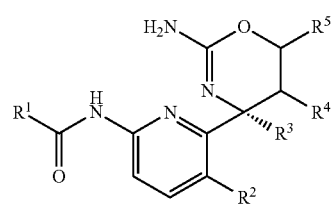

Ia wherein
$R^1$ is selected from the group consisting of
  i) aryl,
  ii) aryl substituted by 1-2 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-2 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
  i) hydrogen,
  ii) $C_{1-6}$-alkyl, and
  iii) halogen;

$R^3$ is selected from the group consisting of
  i) $C_{1-6}$-alkyl, and
  ii) halogen-$C_{16}$-alkyl, $R^4$ is selected from the group consisting of
  i) halogen, and
  ii) hydrogen, $R^5$ is halogen-$C_{1-6}$-alkyl;

or pharmaceutically acceptable salts thereof.

A certain embodiment of the invention provides a compound of formula Ic,

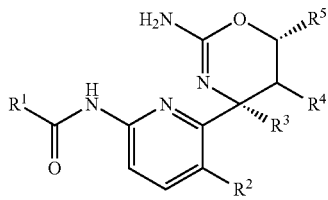

wherein
R¹ is selected from the group consisting of
  i) aryl,
  ii) aryl substituted by 1-4 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
R² is selected from the group consisting of
  i) hydrogen,
  ii) $C_{1-6}$-alkyl, and
  iii) halogen;
R³ is selected from the group consisting of
  i) $C_{1-6}$-alkyl, and
  ii) halogen-$C_{16}$-alkyl,
R⁴ is selected from the group consisting of
  i) halogen, and
  ii) hydrogen,
R⁵ is halogen-$C_{1-6}$-alkyl;
or pharmaceutically acceptable salts thereof.

A certain embodiment of the invention provides a compound of formula Id,

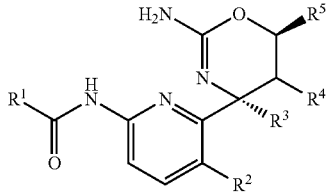

wherein
R¹ is selected from the group consisting of
  i) aryl,
  ii) aryl substituted by 1-4 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
R² is selected from the group consisting of
  i) hydrogen,
  ii) $C_{1-6}$-alkyl, and
  iii) halogen;
R³ is selected from the group consisting of
  i) $C_{1-6}$-alkyl, and
  ii) halogen-$C_{16}$-alkyl,
R⁴ is selected from the group consisting of
  i) halogen, and
  ii) hydrogen,
R⁵ is halogen-$C_{1-6}$-alkyl;
or pharmaceutically acceptable salts thereof.

A certain embodiment of the invention provides a compound of formula Ia-1,

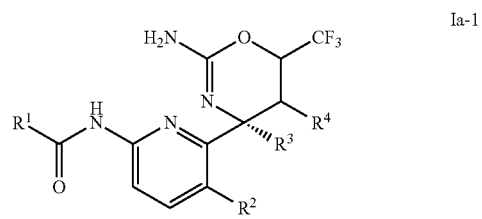

wherein
R¹ is selected from the group consisting of
  i) aryl,
  ii) aryl substituted by 1-2 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-2 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl; and
R³ is selected from the group consisting of
  i) $C_{1-6}$-alkyl, and
  ii) halogen-$C_{16}$-alkyl,
R⁴ is selected from the group consisting of
  i) halogen, and
  ii) hydrogen,
or pharmaceutically acceptable salts thereof.

A certain embodiment of the invention provides a compound of formula I, wherein
R¹ is heteroaryl substituted by 1-2 substituents individually selected from cyano, halogen, halogen-$C_{1-6}$-alkoxy, halogen-$C_{1-6}$-alkyl, $C_{1-6}$-alkoxy, and $C_{1-6}$-alkyl;
R² is hydrogen;
R³ is $C_{1-6}$-alkyl;
R⁴ is selected from the group consisting of
  i) halogen, and
  ii) hydrogen, and
R⁵ is halogen-$C_{1-6}$-alkyl.

A certain embodiment of the invention provides a compound of formula I, wherein
R¹ is heteroaryl substituted by 1-2 substituents individually selected from cyano, halogen, halogen-$C_{1-6}$-alkoxy, halogen-$C_{1-6}$-alkyl, $C_{1-6}$-alkoxy, and $C_{1-6}$-alkyl;
R² is hydrogen;
R³ is $C_{1-6}$-alkyl;
R⁴ is hydrogen; and
R⁵ is halogen-$C_{1-6}$-alkyl.

A certain embodiment of the invention provides a compound of formula I as described herein, wherein $R^1$ is heteroaryl substituted by 1-2 substituents individually selected from amino and cyano.

A certain embodiment of the invention provides a compound of formula I as described herein, wherein $R^1$ is heteroaryl substituted by 1-2 substituents individually selected from cyano, halogen, halogen-$C_{1-6}$-alkoxy, halogen-$C_{1-6}$-alkyl, $C_{1-6}$-alkoxy and $C_{1-6}$-alkyl.

A certain embodiment of the invention provides a compound of formula I as described herein, wherein $R^1$ is pyridinyl, 1H-pyrazolyl or pyrazinyl, each substituted by 1-2 substituents individually selected from cyano, halogen, halogen-$C_{1-6}$-alkoxy, halogen-$C_{1-6}$-alkyl, $C_{1-6}$-alkoxy and $C_{1-6}$-alkyl.

A certain embodiment of the invention provides a compound of formula I as described herein, wherein $R^1$ is 3,5-dichloro-pyridinyl, 3-chloro-5-cyano-pyridinyl, 3-chloro-5-trifluoromethyl-pyridinyl, 4-chloro-1-(difluoromethyl)-1H-pyrazolyl, 5-(difluoromethyl)-pyrazinyl, 5-(fluoromethoxy)pyridinyl, 5-cyano-3-methyl-pyridinyl, 5-cyano-pyridinyl, 5-methoxy-pyrazinyl or 5-methoxy-pyridinyl.

A certain embodiment of the invention provides a compound of formula I as described herein, wherein whenever $R^1$ is heteroaryl it is pyridinyl, 1H-pyrazolyl or pyrazinyl.

A certain embodiment of the invention provides a compound of formula I as described herein, wherein whenever $R^1$ is heteroaryl it is pyridinyl or pyrazinyl.

A certain embodiment of the invention provides a compound of formula I as described herein, wherein whenever $R^1$ is heteroaryl it is pyridinyl.

A certain embodiment of the invention provides a compound of formula I as described herein, wherein $R^1$ is 5-cyano-pyridine-2-yl.

A certain embodiment of the invention provides a compound of formula I as described herein, wherein whenever $R^1$ is heteroaryl it is pyrazinyl.

A certain embodiment of the invention provides a compound of formula I as described herein, wherein whenever $R^1$ is heteroaryl it is 3-amino-pyrazine-2-yl.

A certain embodiment of the invention provides a compound of formula I as described herein, wherein $R^2$ is halogen.

A certain embodiment of the invention provides a compound of formula I as described herein, wherein $R^2$ is F.

A certain embodiment of the invention provides a compound of formula I as described herein, wherein $R^3$ is $C_{1-6}$-alkyl.

A certain embodiment of the invention provides a compound of formula I as described herein, wherein $R^3$ is methyl.

A certain embodiment of the invention provides a compound of formula I as described herein, wherein $R^4$ is halogen.

A certain embodiment of the invention provides a compound of formula I as described herein, wherein $R^4$ is F.

A certain embodiment of the invention provides a compound of formula I as described herein, wherein $R^4$ is hydrogen.

A certain embodiment of the invention provides a compound of formula I as described herein, wherein $R^5$ is fluoro-$C_{1-6}$-alkyl.

A certain embodiment of the invention provides a compound of formula I as described herein, wherein $R^5$ is trifluoromethyl.

A certain embodiment of the invention provides a compound of formula I as described herein, that is selected from the group consisting of N-(6-((4R,5R,6R)-2-amino-5-fluoro-4-methyl-6-(trifluoromethyl)-5,6-dihydro-4H-1,3-oxazin-4-yl)-5-fluoropyridin-2-yl)-5-cyanopicolinamide, N-(6-((4R,5R,6S)-2-amino-5-fluoro-4-methyl-6-(trifluoromethyl)-5,6-dihydro-4H-1,3-oxazin-4-yl)-5-fluoropyridin-2-yl)-5-cyanopicolinamide, N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide, N-(6-((4S,6S)-2-amino-4-methyl-6-(trifluoromethyl)-5,6-dihydro-4H-1,3-oxazin-4-yl)-5-fluoropyridin-2-yl)-3-chloro-5-cyanopicolinamide, N-(6-((4S,6S)-2-amino-4-methyl-6-(trifluoromethyl)-5,6-dihydro-4H-1,3-oxazin-4-yl)-5-fluoropyridin-2-yl)-3-chloro-5-(trifluoromethyl)picolinamide 2,2,2-trifluoroacetate, N-(6-((4S,6S)-2-amino-4-methyl-6-(trifluoromethyl)-5,6-dihydro-4H-1,3-oxazin-4-yl)-5-fluoropyridin-2-yl)-5-methoxypyrazine-2-carboxamide 2,2,2-trifluoroacetate, N-(6-((4S,6S)-2-amino-4-methyl-6-(trifluoromethyl)-5,6-dihydro-4H-1,3-oxazin-4-yl)-5-fluoropyridin-2-yl)-5-cyano-3-methylpicolinamide 2,2,2-trifluoroacetate, N-(6-((4S,6S)-2-amino-4-methyl-6-(trifluoromethyl)-5,6-dihydro-4H-1,3-oxazin-4-yl)-5-fluoropyridin-2-yl)-5-methoxypicolinamide 2,2,2-trifluoroacetate, N-(6-((4S,6S)-2-amino-4-methyl-6-(trifluoromethyl)-5,6-dihydro-4H-1,3-oxazin-4-yl)-5-fluoropyridin-2-yl)-4-chloro-1-(difluoromethyl)-1H-pyrazole-3-carboxamide 2,2,2-trifluoroacetate, N-(6-((4S,6S)-2-amino-4-methyl-6-(trifluoromethyl)-5,6-dihydro-4H-1,3-oxazin-4-yl)-5-fluoropyridin-2-yl)-5-(difluoromethyl)pyrazine-2-carboxamide 2,2,2-trifluoroacetate, N-(6-((4S,6S)-2-amino-4-methyl-6-(trifluoromethyl)-5,6-dihydro-4H-1,3-oxazin-4-yl)-5-fluoropyridin-2-yl)-3,5-dichloropicolinamide 2,2,2-trifluoroacetate, N-(6-((4S,6S)-2-amino-4-methyl-6-(trifluoromethyl)-5,6-dihydro-4H-1,3-oxazin-4-yl)-5-fluoropyridin-2-yl)-5-(fluoromethoxy)picolinamide 2,2,2-trifluoroacetate, and N-(6-((4S,6S)-2-amino-4-methyl-6-(trifluoromethyl)-5,6-dihydro-4H-1,3-oxazin-4-yl)-5-chloropyridin-2-yl)-5-cyanopicolinamide, or pharmaceutically acceptable salts thereof.

A certain embodiment of the invention provides a compound of formula I as described herein, which is N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide or a pharmaceutically acceptable salt thereof.

A certain embodiment of the invention relates to process for preparing a compound of formula I as defined herein, which process comprises reacting a compound of formula XI' with a compound of formula XII' to a compound of formula I

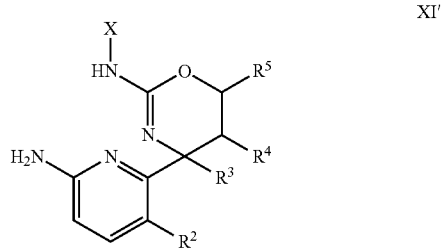

XI'

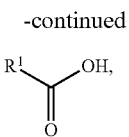

wherein $R^1$, $R^2$, $R^3$, $R^4$ and $R^5$ are as defined herein and X is an amino protecting group.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

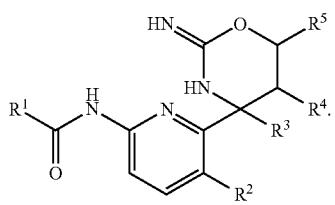

Ie

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Stereoisomers of compounds of formula I are compounds of formula Ia or compounds of formula Ib, in particular compounds of formula Ia, wherein the residues have the meaning as described in any of the embodiments.

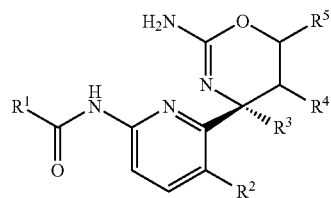

Ia

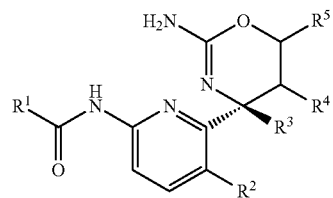

Ib

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the following schemes. The starting material is commercially available or may be prepared in accordance with known methods. Any previously defined residues and variables will continue to have the previously defined meaning unless otherwise indicated.

The compounds of formula I can be prepared through a number of synthetic routes for example as illustrated in schemes 1 and 2. The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of formula I described in the scheme 1 can be isolated and purified by methods known to those skilled in the art, such as but not limited to ion exchange chromatography, solid phase extraction, liquid-liquid extraction, silica chromatography, crystallization and preparative HPLC.

In more detail, compounds of formula I according to the present invention can be prepared by the methods and procedures given below. Some typical procedures for the preparation of compounds of formula I are illustrated in scheme 1.

Scheme 1: Synthesis of compounds I′
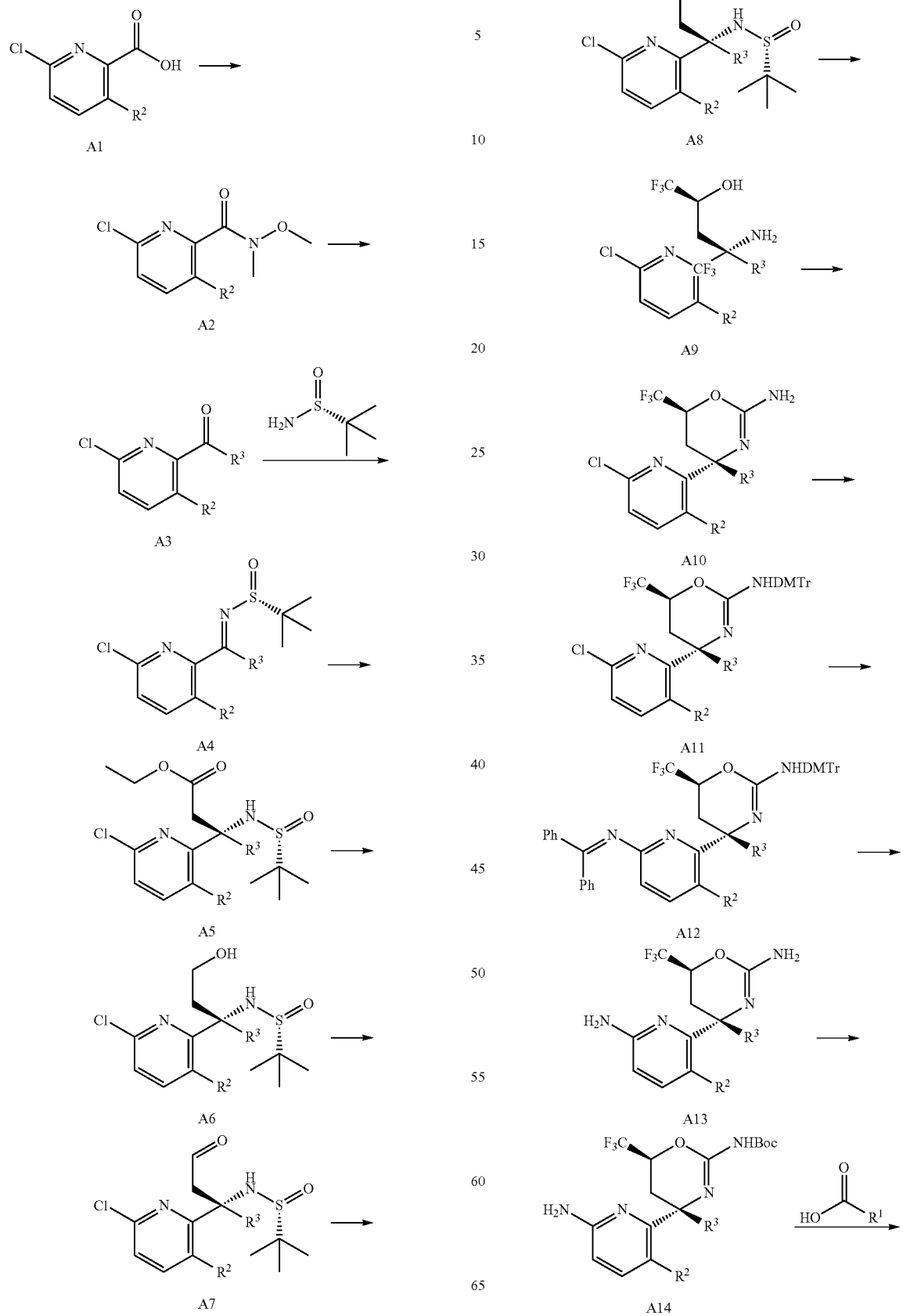

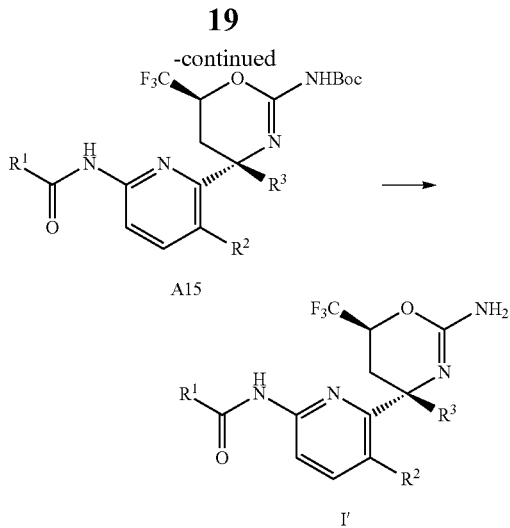

Non commercial ketones of general formula A3 can be synthesized by routes such as depicted in scheme 1 or by other routes known to those skilled in the art. Weinreb amides of formula A2 can be obtained by standard condensation reactions of the acids of formula A1 with N,O-dimethylhydroxylamine or by the intermediate formation of the acyl chloride of acids of formula A1 using an agent such as oxalyl chloride or thionyl chloride using standard conditions such as triethylamine/dichloromethane. The amides of formula A2 can be reacted with organometallics such as methylmagnesium bromide (for $R^3$=Me) in inert aprotic solvents such as tetrahydrofuran or diethyl ether to yield the desired ketones of formula A3.

Intermediate amino alcohols of formula A9 can be prepared in an enantioselective manner as follows: aromatic ketones of formula A3 can be converted into the sulfinyl imine of general formula A4 in analogy to T. P. Tang & J. A. Ellman, J. Org. Chem. 1999, 64, 12, by condensation of the aryl ketone group and a sulfinamide, e.g. an alkyl sulfinamide, in this case most particular (R)-(+)-tert-butylsulfinamide in the presence of a Lewis acid such as e.g. a titanium(IV)alkoxide, more particular titanium(IV)ethoxide in a solvent such as an ether, e.g. diethyl ether or more particular tetrahydrofuran, at temperatures between 23° C. and 70° C.

The conversion of the sulfinyl imine A4 to the sulfinamide ester A5 proceeds stereoselectively by the chiral directing group as described by Tang & Ellman. The sulfinyl imine A4 can be reacted with a titanium enolate generated from e.g. an alkyl acetate, particular ethyl acetate, LDA and chlorotriisopropoxytitanium at low temperature, particular at 78° C. in a solvent such as an ether, e.g. diethyl ether or more particular THF. Alternatively sulfinamide ester A5 can be produced from sulfinyl imine A4 by Reformatsky reaction of a bromoacetic ester derivative and zinc dust, optionally in the presence of copper(I) chloride, in a solvent such as an ether, e.g. diethyl ether or more particular THF, at temperatures from 0 to 70° C., particular at 5 to 10° C.

Chiral sulfinamide ester A5 can be reduced to the chiral alcohol A6 by the reduction of the ethyl ester with an alkali hydride, particular lithium borohydride or lithium aluminum hydride in a solvent such as an ether, e.g. diethyl ether or more particular THF, at temperatures between 0° C. and 50° C., particular at 23° C.

Oxidation of the chiral alcohol A6 to the chiral aldehyde A7 can be achieved by various oxidation methods known to those skilled in the art. DMSO based oxidations, such as the Swern-Moffat oxidation using DMSO, oxalyl chloride and an amine base such as triethylamine or diisopropylethylamine or the Parikh-Doering oxidation using DMSO, sulfur trioxide-pyridine-complex and an amine base such as triethylamine or diisopropylethylamine are particular methods.

The chiral alcohol A8 can be produced by addition of trimethyl(trifluoromethyl)silane (Ruppert-Prakash reagent) to the chiral aldehyde A7 in the presence of a catalytic amount of a fluoride source such as tetrabutylammonium fluoride or tetramethylammonium fluoride in a solvent such as an ether, e.g. diethyl ether or more particular THF, at temperatures from −40 to 23° C., particular at −20 to 0° C. Further addition of a super-stoichiometric amount of tetrabutylammonium fluoride cleaves the initially produced trimethylsilylether of chiral alcohol A8 to the free hydroxyl group. The reaction produces variable ratios of chiral alcohol A8 and the corresponding epimer, which can be separated by chromatography. Further details are given in the experimental section.

Hydrolysis of the chiral directing group in the chiral alcohol A8 to give the chiral amino alcohol A9 can be accomplished with a mineral acid, e.g. sulfuric acid or particular hydrochloric acid in a solvent such as an ether, e.g. 1,4-dioxane or more particular THF, at temperatures between 0° C. and 50° C., particular at 23° C.

The chiral aminooxazines of formula A10 can be prepared by reaction of the chiral amino alcohols of formula A9 with cyanogen bromide in a solvent such as an alcohol, particular ethanol, at temperatures between 23° C. and 100° C., particular at 80° C.

Protection of the amino group in chiral compounds of formula A10, to produce 2-chloropyridines of formula A11 can be performed with triarylmethyl chlorides, such as triphenylmethyl chloride (Tr-Cl), p-methoxyphenyldiphenylmethyl chloride (MMTr-Cl), di(p-methoxyphenyl)phenylmethyl chloride (DMTr-Cl) or tri(p-methoxyphenyl)methyl chloride (TMTr-Cl), particular DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

2-Chloropyridines of formula A11 can be reacted with ammonia equivalents, such as benzophenone imine, in the presence of a suitable transition metal catalyst, such as bis(dibenzylideneacetone)palladium (0) (($dba)_2Pd$) or tris (dibenzylideneacetone)dipalladium (0) (($dba)_3Pd_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula A12.

Deprotection of both amino groups in compounds of formula A12 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the DMTr-group. Then the addition of water or aqueous hydrochloric acid to cleave the benzophenone imine and reaction at ambient temperature produces chiral diamines of formula A13.

The selective protection of the amino group of the 2-aminooxazine residue in diamines of formula A13 to produce compounds of general formula A14, can be performed by reaction with di-tert-butyl dicarbonate under basic conditions, e.g. in the presence of an amine, such as triethylamine or diisopropylethylamine, in a solvent, such as tetrahydrofuran or dichloromethane, at temperatures between 0 to 40° C., particular at ambient temperature.

Amide coupling of 2-aminopyridines of formula A14 and carboxylic acids of formula R2-CO$_2$H to give amides of formula A15 can be effected with condensating agents, such as O-(benzotriazol-1-yl)-N,N,N',N'-tetramethyluronium-hexafluorophosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as dichloromethane, acetonitrile or N,N-dimethylformamide, at temperatures between 0° C. and ambient temperature.

The cleavage of the protecting tert-butoxy carbonyl groups in compounds of formula A15 to produce compounds of general formula I' can be effected by acid, such as trifluoroacetic acid, in inert solvents, such as dichloromethane, at temperatures between 0° C. and ambient temperature.

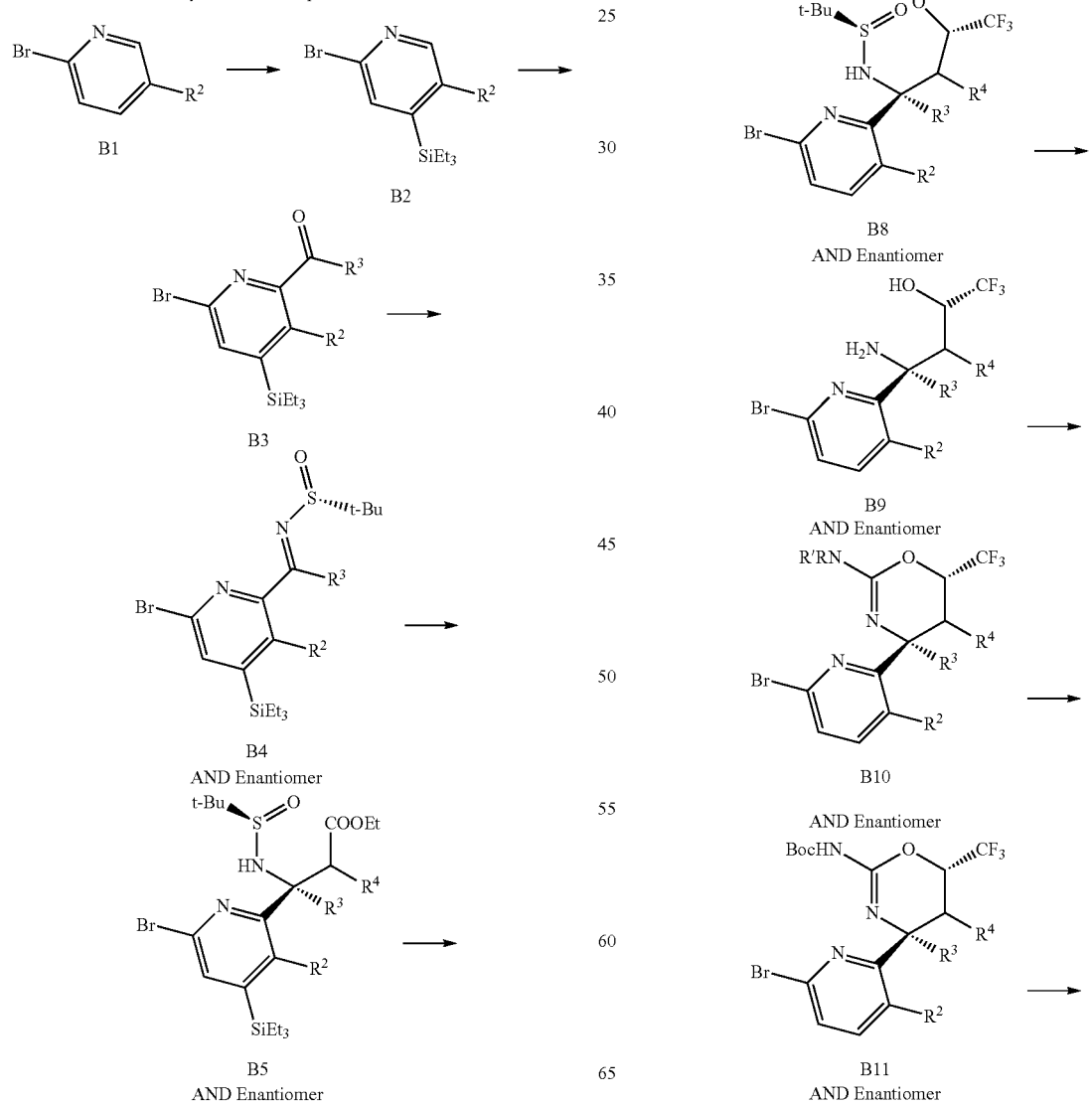

Scheme 2: Alternative synthesis of compounds Ia-1'

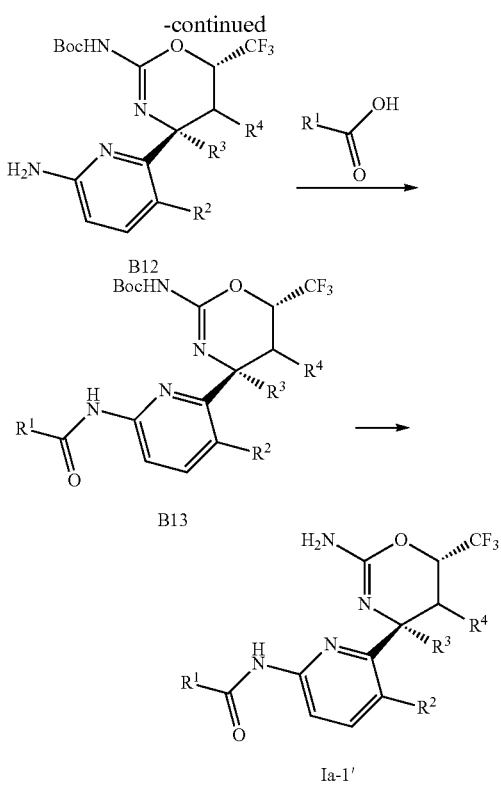

Alternatively the compounds of formula I may be prepared in accordance with scheme 2.

Non-commercial aryl ketones of general formula B3 can be synthesized from the silyl protected pyridine B2 prepared from pyridine B1 by reaction with a strong base, e.g. LDA and an alkylchlorosilane, preferably triethylchlorosilane in an inert aprotic solvents such as tetrahydrofuran or diethyl ether. The protected pyridine B2 can then be reacted again with a strong base, e.g. LDA and an amide, e.g. an acetamide for $R^3$=Me, preferably N,N-dimethylacetamide, in an inert aprotic solvents such as tetrahydrofuran or diethyl ether to give the desired aryl ketone B3.

Sulfinyl imines of formula B4 can be prepared in analogy to T. P. Tang & J. A. Ellman, J. Org. Chem. 1999, 64, 12, by condensation of an aryl ketone of formula B3 and a sulfinamide, e.g. an alkyl sulfinamide, most particularly (R)-tert-butylsulfinamide or (S)-tert-butylsulfinamide, in the presence of a Lewis acid such as e.g. a titanium(IV)alkoxide, more particularly titanium(IV)ethoxide, in a solvent such as an ether, e.g. diethyl ether or more particularly tetrahydrofuran.

The conversion of sulfinyl imines of formula B4 to sulfinamide esters of formula B5 proceeds stereo selectively by the chiral directing group as described by Tang & Ellman. The sulfinyl imines of formula B4 can be reacted in a Reformatsky reaction with a zinc enolate, generated from an alkyl acetate substituted by halogen, e.g. particularly ethyl bromoacetate ($R^4$=H) and ethyl bromofluoroacetate ($R^4$=F), and activated zinc powder at ambient to elevated temperature, particularly at 23 to 60° C., in a solvent such as an ether, e.g. diethyl ether or more particularly tetrahydrofuran, optionally in presence of a copper(I) salt, preferably copper(I) chloride.

Alternatively, the sulfinyl imines of formula B4 can be reacted with a titanium enolate generated from e.g. an alkyl acetate, preferably methyl acetate, LDA and chlorotriisopropoxytitanium at low temperature, preferably at −78° C. in a solvent such as an ether, e.g. diethyl ether or more preferably THF to give B5.

The conversion of the sulfinamide esters of formula B5 to the ester of formula B6 can be effected with tetrabutylammonium fluoride or preferably potassium fluoride in the presence of an acid e.g. acetic acid in an ether or an amide preferably in a mixture of THF and dimethylformamide at ambient to elevated temperature, particularly at 23 to 40° C.

Aldehydes of formula B7 can be prepared by the reduction of ethyl esters of formula B6 with an alkali hydride, e.g. lithium aluminum hydride in presence of diethylamine or sodium dihydrobis(2-methoxyethoxy)aluminate (Red-Al), preferably with diisobutylaluminum hydride (DIBAH) in an inert solvent such as an ether, e.g. diethyl ether or more particularly tetrahydrofuran, or in a chlorinated solvent, such as dichloromethane, at temperatures between 78° C. and ambient temperature.

Alternatively, the aldehydes of formula B7 can be prepared by the reduction of ethyl esters of formula B6 to the corresponding alcohols with an alkali hydride, e.g. lithium aluminum hydride or preferably lithium borohydride in an inert solvent such as an ether, e.g. diethyl ether or more particularly tetrahydrofuran, at temperatures between 0° C. and ambient temperature. The resulting alcohol can be oxidized to the aldehydes of formula B7 by various methods known to someone skilled in the art. DMSO based oxidations, such as the Swern-Moffat oxidation using DMSO, oxalyl chloride and an amine base such as triethylamine or diisopropylethylamine or the Parikh-Doering oxidation using DMSO, sulfur trioxide-pyridine-complex and an amine base such as triethylamine or diisopropylethylamine are particular methods. Another methods is the use of hypervalent iodine reagents, like e.g. the Dess-Martin periodinane in a chlorinated solvent such as dichloromethane at ambient temperature.

Trimethylsilylethers of formula B8 can be obtained by the reaction of aldehydes of formula B7 with a trifluoromethylating agent, preferably trifluoromethyltrimethylsilane (Ruppert-Prakash reagent), in presence of tetrabutylammonium fluoride or preferably tetramethylammonium fluoride in a solvent such as an ether, e.g. diethyl ether or more particularly tetrahydrofuran, at temperatures between −10° C. and ambient temperature.

Hydrolysis of the chiral directing group and the trimethylsilylether of formula B8 to give aminoalcohols of formula B9 can be accomplished with a mineral acid, e.g. sulfuric acid or particularly hydrochloric acid, in a solvent such as an ether, e.g. diethyl ether, tetrahydrofuran or more particularly 1,4-dioxane.

Aminooxazines of formula B10 (R, R'=H) can be prepared by reaction of aminoalcohols of formula B9 with cyanogen bromide in a solvent such as an alcohol, particularly ethanol.

The protection of the amino group of the 2-aminoxazine residue of formula B10 to produce compounds of general formula B11, can be performed by reaction with di-tert-butyl dicarbonate under basic conditions, e.g. in the presence of an amine, such as triethylamine or diisopropylethylamine, in a solvent, such as tetrahydrofuran or dichloromethane, at temperatures between 0 to 40° C., particular at ambient temperature.

Alternatively the compounds of general formula B11 can be prepared by the following sequence: first, aminoalcohols of formula B9 are reacted with an isothiocyanate such as benzoylisothiocyanate (BzNCS) in solvents such as ethyl acetate, tetrahydrofuran or acetonitrile at temperatures between 0° C. and 80° C., preferably 23° C., affords the thiourea alcohols; second, the thiourea alcohols are cyclized to the N-benzoylated oxazines of formula B10 (R=H, R'=Bz) by dehydration through reaction with a carbodiimide, like e.g. dicyclohexylcarbodiimide, diisopropylcarbodiimide or N-(3-dimethylaminopropyl)-N'-ethylcarbodiimide hydrochloride (EDC.HCl), preferably EDC.HCl, in solvents such as ethyl acetate, tetrahydrofuran or acetonitrile, preferably acetonitrile, at temperatures between 23° C. and 100° C., preferably 80° C.; third, the switch of protecting groups from the N-benzoylated oxazines of formula B10 (R═H, R'═Bz) to the N-tert-butoxycarbonylated oxazines of formula B11 can be achieved in a two step procedure by first reaction with di-tert-butyldicarbonate (Boc$_2$O) in the presence of an amine base such as triethylamine or N-ethyl-N,N-diisopropylamine, in a solvent such as dichlormethane, tetrahydrofuran or acetonitrile, at temperatures between 0° C. and 40° C., preferably 23° C., to give the doubly acylated oxazine of formula B10 (R═Boc, R'═Bz), and second selective removal of the benzoyl group by reaction of the doubly acylated oxazine of formula B10 (R═Boc, R'═Bz) with an amine nucleophile, like e.g. diethylamine, dimethylamine or ammonia, preferably ammonia, in a solvent such as dichloromethane or tetrahydrofuran, preferably tetrahydrofuran, at temperatures between 0° C. and 40° C., preferably 23° C.

The conversion of the bromo group in formula B11 to the amine group in formula B12 can be performed by reaction with an azide, in particular sodium azide and a cooper (I) halide in particular copper (I) iodide in the presence of L-ascorbate and an alkyl-1,2-diamine in particular trans-N,N'-dimethylcyclohexane-1,2-diamine in a protic solvent such as an alcohol in particular ethanol and water at elevated temperature preferably approximately 70° C.

The coupling of the aromatic amine B12 with carboxylic acids to give amides of formula B13 can be effected with T3P in an aprotic solvent such as EtOAc at ambient temperature; or alternatively the carboxylic acids can be activated by using reagents such as oxalyl chloride or 1-chloro-N,N,2-trimethyl-1-propenylamine (Ghosez's reagent, CAS-no. 26189-59-3) in a chlorinated solvent such as dichloromethane at 0° C. followed by reaction with the aromatic amine B12 in the presence of an amine base such as triethylamine or diisopropylethylamine at 0° C. to ambient temperature.

The cleavage of the protecting tert-butoxy carbonyl groups in compounds of formula B13 to produce compounds of general formula I that are of formula Ia-1' can be effected by acid, such as trifluoroacetic acid, in inert solvents, such as dichloromethane, at temperatures between 0° C. and ambient temperature.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. A specific salt is trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% CO$_2$ in a humidified incubator, the culture supernatants were harvested for the determination of Aβ 40 concentrations using Perkin-Elmer Human Amyloid beta 1-40 (high specificity) Kit (Cat #AL275C).

In a Perkin-Elmer White Optiplate-384 (Cat #6007290), 2 ul culture supernatants were combined with 2 μl of a 10× AlphaLISA Anti-hAβ Acceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The IC$_{50}$ value were calculated using the Excel XLfit software.

TABLE 1

| Exam. | Structure | BACE1 cell act. Aβ40 IC$_{50}$ [nM] |
|---|---|---|
| | IC$_{50}$ value | |
| 1 | 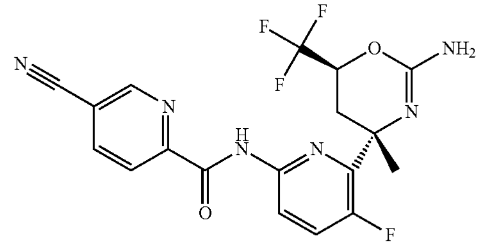 [SMILES: C[C@@]1(c2nc(NC(=O)c3ccc(C#N)cn3)ccc2F)C[C@@H](C(F)(F)F)OC(N)=N1] | 0.0034 |

TABLE 1-continued

| Exam. | Structure | BACE1 cell act. Aβ40 IC$_{50}$ [nM] |
|---|---|---|
| 2 | 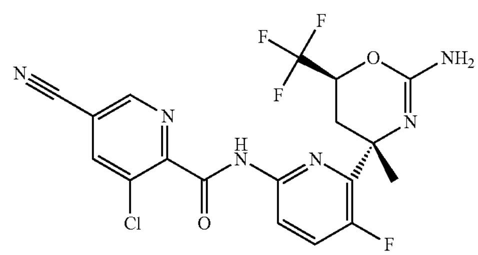 [SMILES: C[C@@]1(c2nc(NC(=O)c3ncc(C#N)cc3Cl)ccc2F)C[C@@H](C(F)(F)F)OC(N)=N1] | 0.0305 |
| 3 | 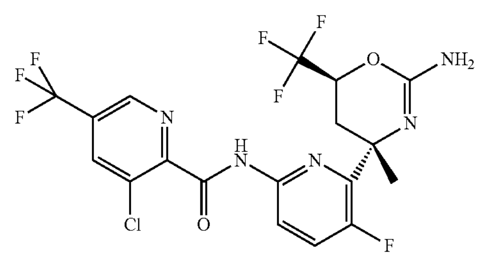 [SMILES: C[C@@]1(c2nc(NC(=O)c3ncc(C(F)(F)F)cc3Cl)ccc2F)C[C@@H](C(F)(F)F)OC(N)=N1] | 0.0396 |
| 4 | 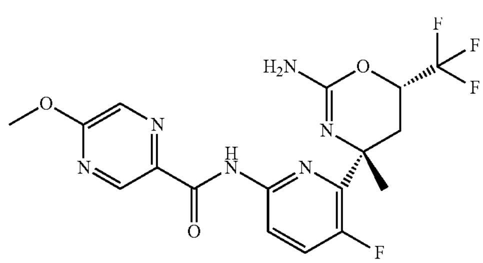 [SMILES: COc1cnc(C(=O)Nc2ccc(F)c([C@@]3(C)C[C@@H](C(F)(F)F)OC(N)=N3)n2)cn1] | 0.3214 |
| 5 | 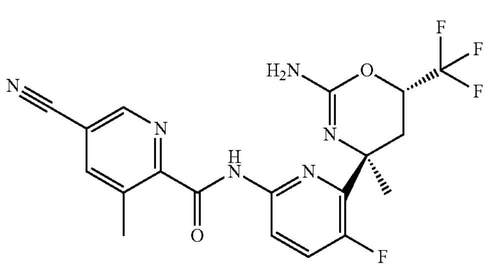 [SMILES: Cc1cc(C#N)cnc1C(=O)Nc1ccc(F)c([C@]2(C)C[C@@H](C(F)(F)F)OC(N)=N2)n1] | 0.039 |
| 6 | 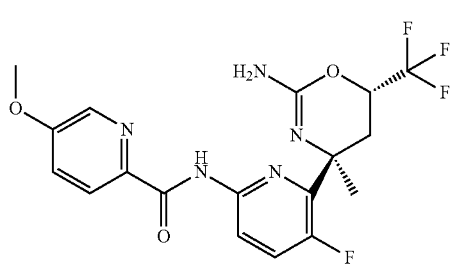 [SMILES: COc1ccc(C(=O)Nc2ccc(F)c([C@]3(C)C[C@@H](C(F)(F)F)OC(N)=N3)n2)nc1] | 0.2235 |

TABLE 1-continued

| | IC$_{50}$ value | |
|---|---|---|
| Exam. | Structure | BACE1 cell act. Aβ40 IC$_{50}$ [nM] |
| 7 | | 0.0368 |
| 8 | | 0.1749 |
| 9 | | 0.286 |
| 10 | | 0.1887 |
| 11 | | 0.062 |

TABLE 1-continued

| Exam. | Structure | BACE1 cell act. Aβ40 IC$_{50}$ [nM] |
|---|---|---|
| 12 | 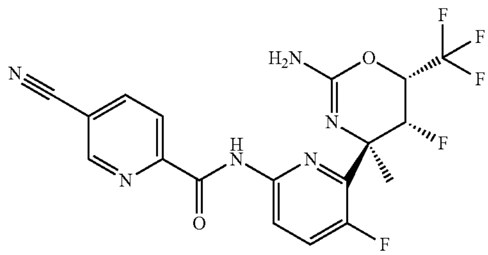 [SMILES: C[C@]1(c2nc(NC(=O)c3ccc(C#N)cn3)ccc2F)N=C(N)O[C@H](C(F)(F)F)[C@@H]1F] | 0.027 |
| 13 | 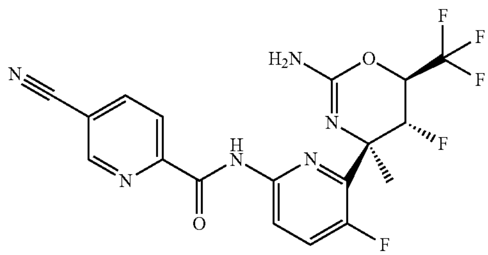 [SMILES: C[C@]1(c2nc(NC(=O)c3ccc(C#N)cn3)ccc2F)N=C(N)O[C@@H](C(F)(F)F)[C@@H]1F] | 0.067 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| | mg/capsule | | | |
|---|---|---|---|---|
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure
The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure
The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |

TABLE 8-continued

| possible sachet composition | |
| --- | --- |
| ingredient | mg/sachet |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General

Abbreviations:

Boc=tert-Butoxycarbonyl, DCM=dichloromethane, EDC.HCl=N-(3-dimethylaminopropyl)-N'-ethylcarbodiimide hydrochloride, EtOAc=Ethyl acetate, HCl=hydrogen chloride, HPLC=high performance liquid chromatography, LDA=lithium diisopropylamide, MS=mass spectrum, THF=tetrahydrofuran, and T3P=2,4,6-Tripropyl-1,3,5,2,4,6-trioxatriphosphorinane-2,4,6-trioxide.

NMR: $^1$H NMR spectra were recorded on a Bruker AC-300 spectrometer at 25° C. with TMS (tetramethylsilane) or residual $^1$H of the given deuterated solvents as internal standards.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

LC-MS (ESI, positive or negative ion) data were recorded on Waters UPLC-MS Systems equipped with Waters Acquity, a CTC PAL auto sampler and a Waters SQD single quadrupole mass spectrometer using ES ionization modes (positive and/or negative). The separation was achieved on a Zorbax Eclipse Plus C18 1.7 μm 2.1×30 mm column at 50° C.; A=0.01% formic acid in water, B=acetonitrile at flow 1; gradient: 0 mM 3% B, 0.2 mM 3% B, 2 min 97% B, 1.7 mM 97% B, 2.0 min 97% B. The injection volume was 2 μL. MS (ESI, positive or negative ion): FIA (flow injection analysis)-MS were recorded on an AppliedBiosystem API150 mass spectrometer. Sample introduction was made with a CTC PAL auto sampler and a Shimadzu LC-10ADVP Pump. The samples were directly flushed to the ESI source of the mass spectrometer with a flow 50 μL/min of a mixture of acetonitrile and 10 mM ammonium acetate (1:1) without a column. The injection volume was 2 μL Synthesis of Intermediates A2

A2a:
6-Chloro-3-fluoro-N-methoxy-N-methylpicolinamide

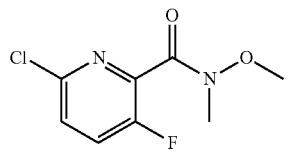

To a magnetically stirred suspension of commercially available 6-chloro-3-fluoropicolinic acid (CAS-no. 884494-76-2) (25 g, 142 mmol, Eq: 1.00) in dichloromethane (430 ml) and N,N-dimethylformamide (100 ml) at room temperature was added N,O-dimethylhydroxylamine hydrochloride (22.2 g, 228 mmol, Eq: 1.6), N-methylmorpholine (23.0 g, 25.1 ml, 228 mmol, Eq: 1.6) and DMAP (1.74 g, 14.2 mmol, Eq: 0.1), cooled to 0° C., added 1-ethyl-3-(3-dimethylaminopropyl)carbodiimid hydrochloride (EDC.HCl) (32.8 g, 171 mmol, Eq: 1.2) and the mixture was allowed to reach ambient temperature over night. After stirring at room temperature for 16 hours the mixture was poured into 1 M HCl, extracted with DCM, washed with sat. NaHCO$_3$-sol., the organic layer was dried over Na$_2$SO$_4$. Removal of the solvent in vacuum left a brown liquid (34.2 g). The crude material was purified by flash chromatography (silica gel, 100 g, 0% to 30% EtOAc in heptane) to give the product, which was triturated with heptane to give the 6-chloro-3-fluoro-N-methoxy-N-methylpicolinamide (29.23 g, 134 mmol, 93.9% yield) as white solid. MS (ISP): m/z=219.4 [M+H]$^+$ and 221.4 [M+2+H]$^+$.

Synthesis of Intermediates A3

A3a: 1-(6-Chloro-3-fluoropyridin-2-yl)ethanone

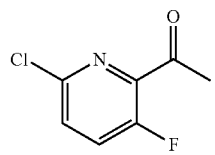

To a solution of 6-chloro-3-fluoro-N-methoxy-N-methylpicolinamide (27.04 g, 124 mmol, Eq: 1.00) in tetrahydrofuran (500 ml) at 0° C. was dropwise added methylmagnesium bromide (3.2 M in 2-methyl-THF) (58.0 ml, 186 mmol, Eq: 1.5) and the mixture was stirred at room temperature for 2 hours. Poured into 3 M HCl, extracted with EtOAc, the organic layer was dried over Na$_2$SO$_4$. Removal of the solvent in vacuum and drying in HV gave the 1-(6-chloro-3-fluoropyridin-2-yl)ethanone (20.86 g, 120 mmol, 97.2% yield) as a light yellow solid. MS (ISP): m/z=174.3 [M+H]$^+$ and 176.3 [M+2+H]$^+$.

Synthesis of Intermediates A4

A4a: (R,E)-N-(1-(6-Chloro-3-fluoropyridin-2-yl)ethylidene)-2-methylpropane-2-sulfinamide

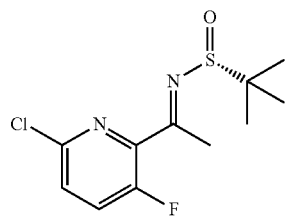 [SMILES: C/C(=N\[S@](=O)C(C)(C)C)c1nc(Cl)ccc1F]

1-(6-Chloro-3-fluoropyridin-2-yl)ethanone (22.6 g, 130 mmol, Eq: 1.00), (R)-2-methylpropane-2-sulfinamide (17.4 g, 143 mmol, Eq: 1.1) and titanium(IV) ethoxide (44.6 g, 41.3 ml, 195 mmol, Eq: 1.5) were dissolved in tetrahydrofuran (250 ml) and the mixture heated to 75° C. and stirred at this temperature over night. The mixture was cooled to 23° C., poured onto sat. NH$_4$Cl-sol., filtered through celite, the solid was washed with ethyl acetate, the filtrate layers were separated, the organic layer was washed with sat. NaHCO$_3$-sol. and brine, dried over Na$_2$SO$_4$. Removal of the solvent left a dark orange solid which was first purified by a short silicagel column filtration to remove residual titanium salts, then by column chromatography (silica gel, 100 g, 0% to 50% ethyl acetate in heptane) to give the (R,E)-N-(1-(6-chloro-3-fluoropyridin-2-yl)ethylidene)-2-methylpropane-2-sulfinamide (32.15 g, 116 mmol, 89.2% yield) as an orange oil. MS (ISP): m/z=277.4 [M+H]$^+$ and 279.4 [M+2+H]$^+$.

Synthesis of Intermediates A5

A5a: (S)-Ethyl 3-(6-chloro-3-fluoropyridin-2-yl)-3-((R)-1,1-dimethylethylsulfinamido)butanoate

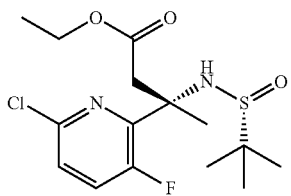 [SMILES: CCOC(=O)C[C@](C)(N[S@](=O)C(C)(C)C)c1nc(Cl)ccc1F]

Activated zinc (11.3 g, 173 mmol, Eq: 3.0) and copper (I) chloride (5.72 g, 57.8 mmol, Eq: 1.00) were suspended in tetrahydrofuran (100 ml) and heated to reflux for 20 min Cooled to 20° C., then a solution of ethyl 2-bromoacetate (24.1 g, 16.0 ml, 145 mmol, Eq: 2.5) in tetrahydrofuran (40.0 ml) was added dropwise and stirring was continued for additional 15 min. A solution of (R,E)-N-(1-(6-chloro-3-fluoropyridin-2-yl)ethylidene)-2-methylpropane-2-sulfinamide (16 g, 57.8 mmol, Eq: 1.00) in tetrahydrofuran (40.0 ml) was then added dropwise between 25° C. to 30° C. Stirring was continued at 23° C. for 1 hour. Then ethanol (4.79 g, 6.08 ml, 104 mmol, Eq: 1.8) was added under ice cooling, filtered all solids off and extracted the filtrate twice with ethyl acetate and sat. NH$_4$Cl-sol. The combined organic layers were washed with water and brine, dried over Na$_2$SO$_4$, filtered and evaporated. The residue was chromatographed with (100 g SiO2, Flashmaster) 0-50% EtOAc in heptane to give (S)-ethyl 3-(6-chloro-3-fluoropyridin-2-yl)-3-((R)-1,1-dimethylethylsulfinamido)butanoate (11.57 g, 31.7 mmol, 54.9% yield) as a yellow oil. MS (ISP): m/z=365.4 [1\4+H]$^+$ and 367.4 [M+2+H]$^+$.

Synthesis of Intermediates A6

A6a: (R)—N—((S)-2-(6-Chloro-3-fluoropyridin-2-yl)-4-hydroxybutan-2-yl)-2-methylpropane-2-sulfinamide

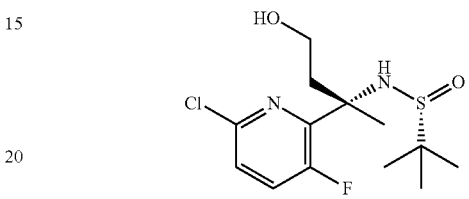

To a solution of (S)-ethyl 3-(6-chloro-3-fluoropyridin-2-yl)-3-((R)-1,1-dimethylethylsulfinamido)butanoate (11.57 g, 31.7 mmol, Eq: 1.00) in tetrahydrofuran (167 ml) at 0° C. was added lithium borohydride (2 M in THF) (23.8 ml, 47.6 mmol, Eq: 1.5), followed by EtOH (1.46 g, 1.85 ml, 31.7 mmol, Eq: 1.00) and the mixture was stirred at room temperature for 1 hour. Poured into sat NH$_4$Cl-sol., extracted with ethyl acetate, the organic layer was dried over Na$_2$SO$_4$. Removal of the solvent in vacuum left a brown oil which was purified by chromatography (silica gel, 100 g, 0% to 100% ethyl acetate in heptane) to give the (R)—N—((S)-2-(6-chloro-3-fluoropyridin-2-yl)-4-hydroxybutan-2-yl)-2-methylpropane-2-sulfinamide (8.85 g, 27.4 mmol, 86.5% yield) as a yellow oil. MS (ISP): m/z=323.4 [M+H]$^+$ and 325.4 [M+2+H]$^+$.

Synthesis of Intermediates A7

A7a: (R)—N—((S)-2-(6-Chloro-3-fluoropyridin-2-yl)-4-oxobutan-2-yl)-2-methylpropane-2-sulfinamide

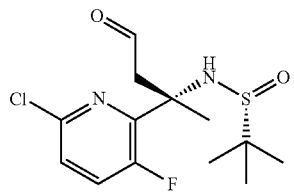 [SMILES: CC(C)(C)[S@@](=O)N[C@@](C)(CC=O)c1nc(Cl)ccc1F]

To a solution of (R)—N—((S)-2-(6-chloro-3-fluoropyridin-2-yl)-4-hydroxybutan-2-yl)-2-methylpropane-2-sulfinamide (3.22 g, 9.97 mmol, Eq: 1.00) in DMSO (20 ml) and triethylamine (6.06 g, 8.34 ml, 59.8 mmol, Eq: 6.0) was added sulfur trioxide-pyridine complex (4.76 g, 29.9 mmol, Eq: 3.0) at 15° C. The mixture was stirred for 2 hours at 23° C. Ice water and 100 ml of sat. NaCl-sol. were added to the reaction mixture, stirred for 10 min, and then extracted twice with ethyl acetate. The organic layers were washed with water and brine, dried over Na$_2$SO$_4$, filtered and evaporated to give a yellow oil. The residue was chromatographed (silica gel, 50 g, 0-80% ethyl acetate in heptane) to give (R)—N—((S)-2-(6-chloro-3-fluoropyridin-2-yl)-4-oxobutan-2-yl)-2-methylpropane-2-sulfinamide (2.96 g, 9.23 mmol, 92.5% yield) as a light yellow oil. MS (ISP): m/z=321.5 [M+H]⁺ and 323.5 [M+H]⁺.

Synthesis of Intermediates A8

A8a: (R)—N-((2S,4S)-2-(6-Chloro-3-fluoropyridin-2-yl)-5,5,5-trifluoro-4-hydroxypentan-2-yl)-2-methylpropane-2-sulfinamide and (R)—N-((2S,4R)-2-(6-chloro-3-fluoropyridin-2-yl)-5,5,5-trifluoro-4-hydroxypentan-2-yl)-2-methylpropane-2-sulfinamide

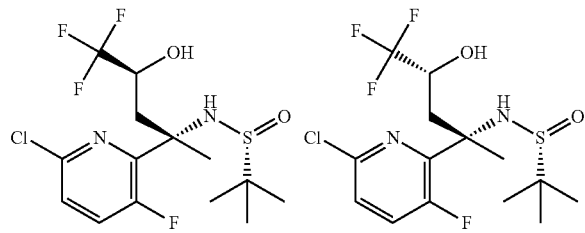

To a solution of (R)—N—((S)-2-(6-chloro-3-fluoropyridin-2-yl)-4-oxobutan-2-yl)-2-methylpropane-2-sulfinamide (2.96 g, 9.23 mmol, Eq: 1.00) in tetrahydrofuran (50 ml) was added at 0° C. (trifluoromethyl)trimethylsilane (1.97 g, 2.04 ml, 13.8 mmol, Eq: 1.5) dropwise. Then was added tetramethylammonium fluoride (172 mg, 1.85 mmol, Eq: 0.2) at 0° C. and the brown solution was stirred at 0° C. for 10 min, removed the ice bath, the solution was allowed to reach room temperature and stirring was continued for 2 hours. Then tetrabutylammonium fluoride (1 M in THF) (10.1 ml, 10.1 mmol, Eq: 1.1) was added dropwise and the mixture was stirred at ambient temperature for another 2 hours. Poured into sat. NaHCO₃-sol. and ice, extracted with ethyl acetate, washed the organic layers with brine, dried over Na₂SO₄ and filtered off. Removal of solvent in vacuum left a light yellow oil, which was purified by flash chromatography (silica gel, 50 g, 0-80% ethyl acetate in heptane) which left (R)—N-((2S,4S)-2-(6-chloro-3-fluoropyridin-2-yl)-5,5,5-trifluoro-4-hydroxypentan-2-yl)-2-methylpropane-2-sulfinamide (710 mg, 1.82 mmol, 19.7% yield; less polar isomer) and (R)—N-((2S,4R)-2-(6-chloro-3-fluoropyridin-2-yl)-5,5,5-trifluoro-4-hydroxypentan-2-yl)-2-methylpropane-2-sulfinamide (580 mg, 1.48 mmol, 16.1% yield; more polar isomer), both as brown oils. MS (ISP): m/z=391.5 [M+H]⁺ and 393.5 [M+H]⁺.

Synthesis of Intermediates A9

A9a: (2S,4S)-4-Amino-4-(6-chloro-3-fluoropyridin-2-yl)-1,1,1-trifluoropentan-2-ol

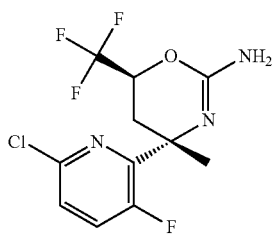 [SMILES: C[C@@]1(c2nc(Cl)ccc2F)C[C@@H](C(F)(F)F)OC(N)=N1]

To a solution of (R)—N-((2S,4S)-2-(6-chloro-3-fluoropyridin-2-yl)-5,5,5-trifluoro-4-hydroxypentan-2-yl)-2-methylpropane-2-sulfinamide (710 mg, 1.82 mmol, Eq: 1.00) in tetrahydrofuran was added at ambient temperature conc. HCl (37% in water) (537 mg, 448 µl, 5.45 mmol, Eq: 3.0). The brown reaction solution was stirred at 23° C. for 2 hours. Poured into sat. NaHCO₃-sol., extracted with ethyl acetate, washed organic layer with brine, dried over Na₂SO₄. Removal of the solvent in vacuum left a light brown oil which was purified by chromatography (silica gel, 10 g, 0-50% ethyl acetate in heptane) to give (2S,4S)-4-amino-4-(6-chloro-3-fluoropyridin-2-yl)-1,1,1-trifluoropentan-2-ol (264 mg, 921 µmol, 50.7% yield) as a brown oil. MS (ISP): m/z=287.4 [M+H]⁺ and 289.5 [M+2+H]⁺.

Synthesis of Intermediates A10

A10a: (4S,6S)-4-(6-Chloro-3-fluoropyridin-2-yl)-4-methyl-6-(trifluoromethyl)-5,6-dihydro-4H-1,3-oxazin-2-amine

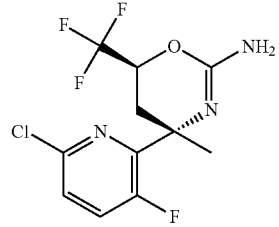 [SMILES: C[C@@]1(c2nc(Cl)ccc2F)C[C@@H](C(F)(F)F)OC(N)=N1]

To a solution of (2S,4S)-4-amino-4-(6-chloro-3-fluoropyridin-2-yl)-1,1,1-trifluoropentan-2-ol (262 mg, 914 µmol, Eq: 1.00) in ethanol (5 ml) was added under argon at ambient temperature sodium bicarbonate (30.7 mg, 366 µmol, Eq: 0.4) and cyanogen bromide (290 mg, 2.74 mmol, Eq: 3.00). The brown reaction solution was stirred at 80° C. in a sealed tube for 20 hours. Poured into ice water and sat. NaHCO₃-sol., then extracted with ethyl acetate. The organic layer was dried over Na₂SO₄, filtered and evaporated. The residue was purified by chromatography (silica gel, 10 g, 0-80% ethyl acetate in heptane) to give (4S,6S)-4-(6-chloro-3-fluoropyridin-2-yl)-4-methyl-6-(trifluoromethyl)-5,6-dihydro-4H-1,3-oxazin-2-amine (170 mg, 436 µmol, 47.7% yield) as a light brown solid. MS (ISP): m/z=312.5 [M+H]⁺ and 314.5 [M+2+H]⁺.

Synthesis of Intermediates A11

A11a: (4S,6S)—N-(bis(4-methoxyphenyl)(phenyl)methyl)-4-(6-chloro-3-fluoropyridin-2-yl)-4-methyl-6-(trifluoromethyl)-5,6-dihydro-4H-1,3-oxazin-2-amine

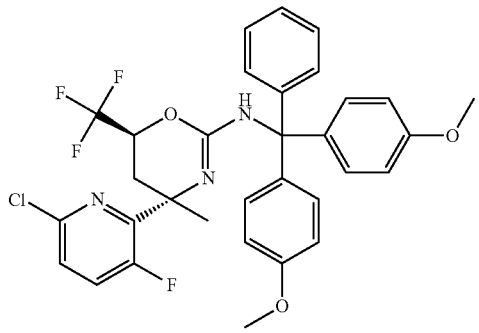 [SMILES: COc1ccc(C(NC2=N[C@](C)(c3nc(Cl)ccc3F)C[C@@H](C(F)(F)F)O2)(c2ccccc2)c2ccc(OC)cc2)cc1]

To a solution of (4S,6S)-4-(6-chloro-3-fluoropyridin-2-yl)-4-methyl-6-(trifluoromethyl)-5,6-dihydro-4H-1,3-oxazin-2-amine (170 mg, 436 µmol, Eq: 1.00) in dichloromethane (10 ml) and diisopropylethylamine (113 mg, 152 µl, 873 µmol, Eq: 2.0) was added at ambient temperature 4,4'-dimethoxytrityl chloride (222 mg, 655 µmol, Eq: 1.5). The reaction solution was stirred at 23° C. for 4 hours. The reaction mixture was washed with water and brine. The organic layer was dried over Na$_2$SO$_4$, filtered and evaporated. The residue was purified by chromatography (silica gel, 10 g, 0-50% ethyl acetate in heptane) to give (4S,6S)—N-(bis(4-methoxyphenyl)(phenyl)methyl)-4-(6-chloro-3-fluoropyridin-2-yl)-4-methyl-6-(trifluoromethyl)-5,6-dihydro-4H-1,3-oxazin-2-amine (163 mg, 265 µmol, 60.8% yield) as an off-white foam. MS (ISP): m/z=615.1 [M+H]$^+$ and 617.2 [M+2+H]$^+$.

Synthesis of Intermediates A12

A12a: (4S,6S)—N-(bis(4-methoxyphenyl)(phenyl)methyl)-4-(6-(diphenylmethyleneamino)-3-fluoropyridin-2-yl)-4-methyl-6-(trifluoromethyl)-5,6-dihydro-4H-1,3-oxazin-2-amine

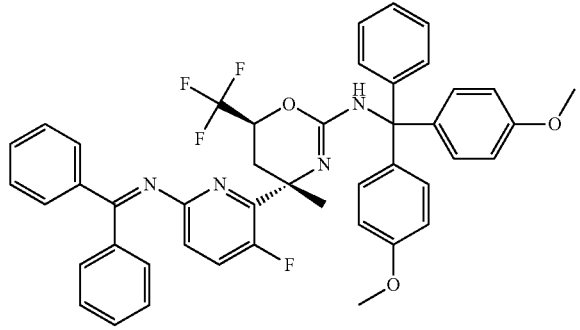 [SMILES: COc1ccc(C(NC2=N[C@](C)(c3nc(N=C(c4ccccc4)c4ccccc4)ccc3F)C[C@@H](C(F)(F)F)O2)(c2ccccc2)c2ccc(OC)cc2)cc1]

Under argon in a sealed tube were added to a solution of (4S,6S)—N-(bis(4-methoxyphenyl)(phenyl)methyl)-4-(6-chloro-3-fluoropyridin-2-yl)-4-methyl-6-(trifluoromethyl)-5,6-dihydro-4H-1,3-oxazin-2-amine (160 mg, 261 µmol, Eq: 1.00) in toluene (3 ml) sodium tert-butoxide (75.1 mg, 782 µmol, Eq: 3.00), 2-dicyclohexylphosphino-2',4',6'-triisopropylbiphenyl (X-Phos) (18.6 mg, 39.1 µmol, Eq: 0.15) and tris(dibenzylideneacetone)dipalladium(0) (11.9 mg, 13.0 µmol, Eq: 0.05). benzophenone imine (94.4 mg, 87.5 µl, 521 µmol, Eq: 2.00) was added finally via syringe. The tube was sealed under argon and the mixture was stirred at 85° C. for 3.5 hours. After cooling to ambient temperature the brown solution was extracted with ethyl acetate and water. The organic layer was washed with brine, dried over Na$_2$SO$_4$, filtered and evaporated to give a brown oil. The residue was purified by chromatography (silica gel, 10 g, 0-50% ethyl acetate in heptane) to give (4S,6S)—N-(bis(4-methoxyphenyl)(phenyl)methyl)-4-(6-(diphenylmethyleneamino)-3-fluoropyridin-2-yl)-4-methyl-6-(trifluoromethyl)-5,6-dihydro-4H-1,3-oxazin-2-amine (123 mg, 162 µmol, 62.2% yield) as a light yellow foam. MS (ISP): m/z=759.3 [M+H]$^+$.

Synthesis of Intermediates A13

A13a: (4S,6S)-4-(6-Amino-3-fluoropyridin-2-yl)-4-methyl-6-(trifluoromethyl)-5,6-dihydro-4H-1,3-oxazin-2-amine

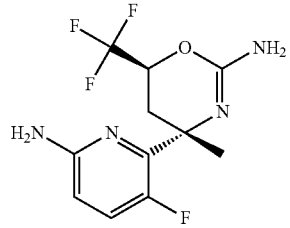 [SMILES: C[C@@]1(c2nc(N)ccc2F)C[C@@H](C(F)(F)F)OC(N)=N1]

To a solution of (4S,6S)—N-(bis(4-methoxyphenyl)(phenyl)methyl)-4-(6-(diphenylmethyleneamino)-3-fluoropyridin-2-yl)-4-methyl-6-(trifluoromethyl)-5,6-dihydro-4H-1,3-oxazin-2-amine (122 mg, 161 µmol, Eq: 1.00) in dichloromethane (10 ml) was added at ambient temperature trifluoroacetic acid (1.83 g, 1.24 ml, 16.1 mmol, Eq: 100). The orange reaction solution was stirred at 23° C. for 1 hour and then evaporated. The residue was dissolved in dioxane (20 ml) and 1 N HCl (3.22 ml, 3.22 mmol, Eq: 20) was added. Stirring was continued at 23° C. for 3 hours. Poured into 1 M Na$_2$CO$_3$, extracted twice with ethyl acetate, washed the combined organic layers with water and brine, dried over Na$_2$SO$_4$ and filtered. Removal of the solvent in vacuum left a brown oil which was purified by chromatography (silica gel, 5 g; ethyl acetate/MeOH 8:1) to give (4S,6S)-4-(6-amino-3-fluoropyridin-2-yl)-4-methyl-6-(trifluoromethyl)-5,6-dihydro-4H-1,3-oxazin-2-amine (35 mg, 120 µmol, 74.5% yield) as an off-white foam. MS (ISP): m/z=293.5 [M+H]$^+$.

Synthesis of Intermediates A14

A14a: tert-Butyl (4S,6S)-4-(6-amino-3-fluoropyridin-2-yl)-4-methyl-6-(trifluoromethyl)-5,6-dihydro-4H-1,3-oxazin-2-ylcarbamate

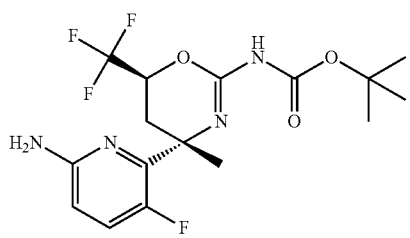 [SMILES: CC(C)(C)OC(=O)NC1=N[C@](C)(c2nc(N)ccc2F)C[C@@H](C(F)(F)F)O1]

To a solution of (4S,6S)-4-(6-amino-3-fluoropyridin-2-yl)-4-methyl-6-(trifluoromethyl)-5,6-dihydro-4H-1,3-oxazin-2-amine (32 mg, 110 µmol, Eq: 1.00) in dichloromethane (1 ml) and diisopropylethylamine (19.8 mg, 26.8 µl, 153 µmol, Eq: 1.4) was added at rt di-tert-butyl dicarbonate (Boc$_2$O) (28.7 mg, 131 µmol, Eq: 1.2). The clear, colourless reaction solution was stirred at 23° C. for 20 hours. All volatiles were removed in vacuum and the residue was purified by chromatography (silica gel, 10 g; ethyl acetate/MeOH 8:1) to give tert-butyl (4S,6S)-4-(6-amino-3-fluoropyridin-2-yl)-4-methyl-6-(trifluoromethyl)-5,6-dihydro-4H-1,3-oxazin-2-ylcarbamate (41.3 mg, 105 µmol, 96.1% yield) as a white foam. MS (ISP): m/z=393.4 [M+H]$^+$.

Synthesis of Intermediates A15

A15a: tert-Butyl (4S,6S)-4-(6-(5-cyanopicolinamido)-3-fluoropyridin-2-yl)-4-methyl-6-(trifluoromethyl)-5,6-dihydro-4H-1,3-oxazin-2-ylcarbamate

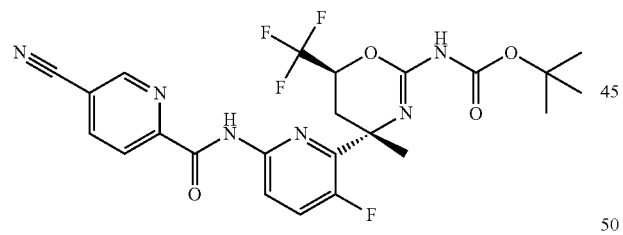

5-Cyanopicolinic acid (19.4 mg, 131 µmol, Eq: 1.30) was dissolved in dichloromethane (0.8 ml) and DMF (0.4 ml), then diisopropylethylamine (39.0 mg, 52.7 µl, 302 µmol, Eq: 3.00) and (dimethylamino)-N,N-dimethyl(3H-[1,2,3]triazolo[4,5-b]pyridin-3-yloxy)methaniminium hexafluorophosphate (HATU) (57.4 mg, 151 µmol, Eq: 1.50) were added at ambient temperature. The resulting yellow solution was stirred for 10 min then a solution of tert-butyl (4S,6S)-4-(6-amino-3-fluoropyridin-2-yl)-4-methyl-6-(trifluoromethyl)-5,6-dihydro-4H-1,3-oxazin-2-ylcarbamate (39.5 mg, 101 µmol, Eq: 1.00) in dichloromethane (0.8 ml) was added. The brown reaction solution was stirred at 23° C. for 16 hours. The reaction mixture was poured into ice cold sat. NaHCO$_3$ solution and extracted twice with dichloromethane. The organic layers were washed with brine, dried over Na$_2$SO$_4$, filtered and evaporated. The residue was purified by chromatography (silica gel, 5 g, 0-50% ethyl acetate in heptane) to give tert-butyl (4S,6S)-4-(6-(5-cyanopicolinamido)-3-fluoropyridin-2-yl)-4-methyl-6-(trifluoromethyl)-5,6-dihydro-4H-1,3-oxazin-2-ylcarbamate (16 mg, 30.6 µmol, 30.4% yield) as a colourless oil. MS (ISP): m/z=523.6 [M+H]$^+$.

Synthesis of the intermediate pyridine B2b (R$^2$=Cl): 2-Bromo-5-chloro-4-(triethylsilyl)pyridine

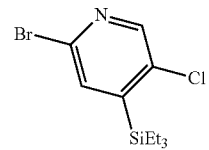

To a solution of diisopropylamine (10.6 g) in THF (170 ml) was added at 20° C. n-butyl lithium (1.6 M in hexane, 65.6 ml) over 30 min and the solution was allowed to warm to 0° C. and stirring was continued for 30 min. The solution was cooled again to 78° C. and treated with a solution of 2-bromo-5-chloropyridine (19.2 g) in THF (30 ml) over 15 min and stirring was continued for 1 h. To the dark brown solution was added triethylchlorosilane (16.6 g) over 3 min, the mixture was warm to 20° C. and was poured into a mixture of aqueous HCl (1 M, 110 ml) and half-saturated aqueous NH$_4$Cl (110 ml) and extracted with t-butylmethyl ether (300 ml). The organic layer was washed with brine, dried, evaporated and the residue purified by flash chromatography (SiO$_2$, gradient of EtOAc in heptane, 0 to 20% EtOAc) to give the title compound (30.7 g, 86%) as a pale yellow liquid. MS (ESI): m/z=306.3, 308.3, 310.3 [M+H]$^+$.

Synthesis of the intermediate ketone B3b (R$^2$=Cl): 1-(6-Bromo-3-chloro-4-(triethylsilyl)pyridin-2-yl)ethanone

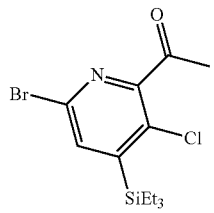

To a solution of diisopropylamine (17.2 g) in THF (400 ml) was added at 20° C. n-butyl lithium (1.6 M in hexane, 106 ml) over 30 min and the solution was allowed to warm to 0° C. and stirring was continued for 30 min. The solution was cooled again to 78° C. and treated with a solution of 2-bromo-5-chloro-4-(triethylsilyl)pyridine B2b (40.0 g) in THF (40 ml) over 15 min and stirring was continued for 15 min. To the dark red solution was added N,N-dimethylacetamide (14.8 g) over 2 min and stirring was continued for 20 min. The mixture was warm to 40° C., poured into a mixture of aqueous HCl (1 M, 200 ml) and brine (200 ml) and extracted with t-butylmethyl ether. The organic layer was washed with brine, dried and evaporated to give the crude title compound as a brown oil (41.5 g).

Synthesis of the Intermediate Sulfinyl Imines B4

B4a (R² = F): (R,E)-N-(1-(6-Bromo-3-fluoro-4-(triethylsilyl)pyridin-2-yl)ethylidene)-2-methylpropane-2-sulfinamide

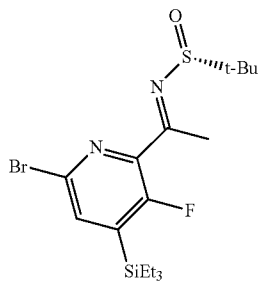

To a solution of 1-(6-bromo-3-fluoro-4-(triethylsilyl)pyridin-2-yl)ethanone, prepared according to Badiger, S. et al., int. patent application WO 2012095469A1, (8.13 g) in THF (59 ml) was added subsequently at 22° C. (R)-(+)-tert-butylsulfinamide (3.26 g) and titanium(IV)ethoxide (11.2 g) and the solution was stirred at 60° C. for 6 h. The mixture was cooled to 22° C., treated with brine, the suspension was stirred for 10 min and filtered over dicalite. The layers were separated, the aqueous layer was extracted with ethyl acetate, the combined organic layers were washed with water, dried and evaporated. The residue was purified by flash chromatography (SiO₂, n-heptane/EtOAc, 5:1) to give the title compound (7.5 g, 70%) as a yellow oil. MS (ESI): m/z=435.3, 437.3 [M+H]⁺.

B4b (R² = Cl): (R,E)-N-(1-(6-Bromo-3-chloro-4-(triethylsilyl)pyridin-2-yl)ethylidene)-2-methylpropane-2-sulfinamide

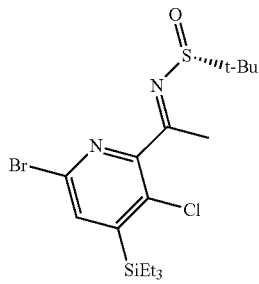

Crude 1-(6-bromo-3-chloro-4-(triethylsilyl)pyridin-2-yl)ethanone B3b (41.5 g) was reacted with (R)-(+)-tert-butylsulfinamide in analogy to the preparation of compound B4a to give after purification by flash chromatography (SiO₂, gradient of EtOAc in heptane, 0-10% EtOAc) the title compound (18.0 g) as an orange oil. MS (ESI): m/z=451.1, 453.1, 455.1 [M+H]⁺.

Synthesis of the Intermediate Sulfinamide Esters B5

B5a (R² = F): (S)-Ethyl 3-(6-bromo-3-fluoro-4-(triethylsilyl)pyridin-2-yl)-3-((R)-1,1-dimethylethylsulfinamido)butanoate

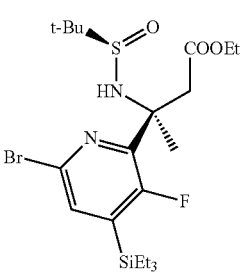

To a solution of diisopropylamide (9.41 g) in THF (325 ml) was added at 20° C. n-butyllithium (1.6 M solution in hexane, 58.1 ml) and stirring was continued at 0° C. for 30 min. The solution was cooled to 78° C., treated with ethyl acetate (8.19 g) keeping the temperature below −70° C. and stirring was continued at −78° C. for 30 min. A solution of chlorotriisopropoxytitanium (24.2 g) in THF (65 ml) was added and stirring was continued at 78° C. for 30 min. The mixture was treated with a solution of (R,E)-N-(1-(6-bromo-3-fluoro-4-(triethylsilyl)pyridin-2-yl)ethylidene)-2-methylpropane-2-sulfinamide B4a (13.5 g) in THF (65 ml) and stirring was continued at −78° C. for 1 h. The mixture was quenched with saturated aqueous NH₄Cl solution, filtered over dicalite, the organic layer was washed with water, dried, evaporated and the residue purified by flash chromatography (SiO₂, gradient of n-heptane/EtOAc (5 to 45% EtOAc) to give the title compound (11.5 g, 71%) as a pale yellow oil. MS (ESI): m/z=523.6, 525.6 [M+H]⁺.

B5b (R² = Cl): (S)-Ethyl 3-(6-bromo-3-chloro-4-(triethylsilyl)pyridin-2-yl)-3-((R)-1,1-dimethylethylsulfinamido)butanoate

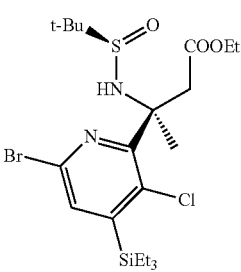

(R,E)-N-(1-(6-Bromo-3-chloro-4-(triethylsilyl)pyridin-2-yl)ethylidene)-2-methylpropane-2-sulfinamide B4b (14.0 g) was reacted with ethyl acetate in analogy to the preparation of compound B5a to give after purification by flash chromatography (SiO₂, gradient of EtOAc in heptane, 0-50% EtOAc) the title compound (6.1 g) as an orange oil. MS (ESI): m/z=539.2, 541.2, 543.2 [M+H]⁺. A second fraction contained the starting material (7.44 g).

B5c (R², R⁴=F): (2R,3R)-Ethyl 3-(6-bromo-3-fluoropyridin-2-yl)-3-((R)-1,1-dimethylethylsulfinamido)-2-fluorobutanoate

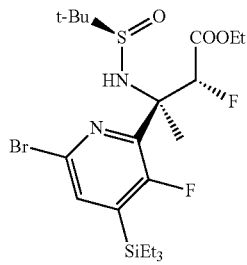

Activated zinc (3.33 g, 51.0 mmol) was suspended in tetrahydrofuran (90 ml) and heated to reflux. A solution of ethyl 2-bromo-2-fluoroacetate (9.43 g, 6.03 ml, 51.0 mmol) and (R,E)-N-(1-(6-bromo-3-fluoro-4-(triethylsilyl)pyridin-2-yl)ethylidene)-2-methylpropane-2-sulfinamide (11.1 g, 25.5 mmol) in tetrahydrofuran (50 ml) was added drop wise and stirred an additional hour at 70° C. Removed from oilbath and the reaction was quenched by drop wise addition of ethanol (2 ml), filtered through Celite and extracted with EtOAc and sat NH₄Cl-sol., dried over Na₂SO₄, filtered and evaporated. The crude material was purified by flash chromatography (silica gel, 50 g, 0% to 50% EtOAc in heptane) to give the (2R,3R)-ethyl 3-(6-bromo-3-fluoro-4-(triethylsilyl)pyridin-2-yl)-3-((R)-1,1-dimethylethylsulfinamido)-2-fluorobutanoate (9.9 g, 18.3 mmol, 71.7% yield) as a yellow oil. MS (ESI): m/z=541.6, 543.6 [M+H]⁺.

Synthesis of the Intermediate Esters B6

B6a (R²=F): (S)-Ethyl 3-(6-bromo-3-fluoropyridin-2-yl)-3-((R)-1,1-dimethylethylsulfinamido)butanoate

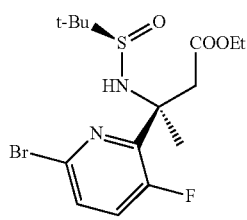 [SMILES: CCOC(=O)C[C@](C)(N[S@](=O)C(C)(C)C)c1nc(Br)ccc1F]

To a solution of (S)-ethyl 3-(6-bromo-3-fluoro-4-(triethylsilyl)pyridin-2-yl)-3-((R)-1,1-dimethylethylsulfinamido)butanoate B5a (11.5 g) in THF (100 ml) was added subsequently at 22° C. acetic acid (2.64 g), KF (2.55 g) and DMF (100 ml) and stirring was continued at 22° C. for 2 h and at 40° C. for 30 min. The mixture was partitioned between EtOAc (600 ml) and aqueous saturated NaHCO₃-sol. (600 ml), the organic layer was washed with brine, dried and evaporated (50° C., 2 mbar) to give the crude title compound (9.27 g) as a pale yellow oil. MS (ESI): m/z=409.5, 411.5 [M+H]⁺.

B6b (R²=Cl): (S)-Ethyl 3-(6-bromo-3-chloropyridin-2-yl)-3-((R)-1,1-dimethylethylsulfinamido)butanoate

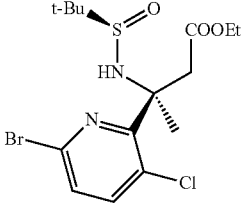 [SMILES: CCOC(=O)C[C@](C)(N[S@](=O)C(C)(C)C)c1nc(Br)ccc1Cl]

(S)-Ethyl 3-(6-bromo-3-chloro-4-(triethyl silyl)pyridin-2-yl)-3-((R)-1,1-dimethylethylsulfinamido)butanoate B5b (3.7 g) was reacted with KF in analogy to the preparation of compound B6a to give the crude title compound (3.05 g) as an light brown oil. MS (ESI): m/z=425.1, 427.1, 429.1 [M+H]⁺.

B6c (R², R⁴=F): (2R,3R)-Ethyl 3-(6-bromo-3-fluoropyridin-2-yl)-3-((R)-1,1-dimethylethylsulfinamido)-2-fluorobutanoate

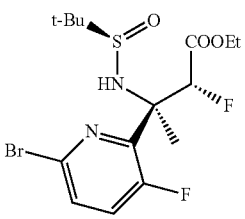 [SMILES: CCOC(=O)[C@H](F)[C@](C)(N[S@](=O)C(C)(C)C)c1nc(Br)ccc1F]

To a solution of (2R,3R)-ethyl 3-(6-bromo-3-fluoro-4-(triethylsilyl)pyridin-2-yl)-3-((R)-1,1-dimethylethylsulfinamido)-2-fluorobutanoate B5c (10.5 g, 19.4 mmol) in N,N-dimethylformamide (105 ml) and tetrahydrofuran (105 ml) at room temperature was added dry potassium fluoride (2.25 g, 38.8 mmol) and acetic acid (1.16 g, 1.11 ml, 19.4 mmol,) and the mixture was stirred at room temperature for 3 hours. Poured into sat NaHCO₃-sol., extracted with EtOAc, the organic layer was dried over Na₂SO₄. Removal of the solvent in vacuum left the (2R,3R)-ethyl 3-(6-bromo-3-fluoropyridin-2-yl)-3-((R)-1,1-dimethylethylsulfinamido)-2-fluorobutanoate (6 g, 14.0 mmol, 72.4% yield) as a light yellow oil. MS (ESI): m/z=427.5, 429.5 [M+H]⁺.

Synthesis of the Intermediate Aldehydes B7

B7a (R²=F): (R)—N—((S)-2-(6-Bromo-3-fluoropyridin-2-yl)-4-oxobutan-2-yl)-2-methylpropane-2-sulfinamide

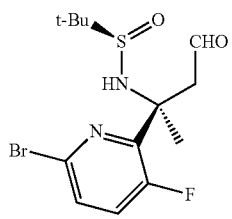 [SMILES: CC(C)(C)[S@@](=O)N[C@@](C)(CC=O)c1nc(Br)ccc1F]

To a solution of crude (S)-ethyl 3-(6-bromo-3-fluoropyridin-2-yl)-3-((R)-1,1-dimethylethylsulfinamido)butanoate B6a (8.8 g) in dichloromethane (220 ml) was added at 78° C. diisobutylaluminum hydride (1 M in toluene, 49 ml) over 15 min and stirring was continued for 1 h. The mixture was treated with aqueous saturated NH₄Cl, warmed to 23° C., filtered through dicalite, the organic layer was dried, evaporated and the residue purified by flash chromatography (SiO₂, gradient of EtOAc in heptane, 5 to 100% EtOAc) to give the title (4.0 g, 51%) as a colorless oil. MS (ESI): m/z=365.3, 367.3 [M+H]⁺.

B7b (R²=Cl): (R)—N—((S)-2-(6-bromo-3-chloropyridin-2-yl)-4-oxobutan-2-yl)-2-methylpropane-2-sulfinamide

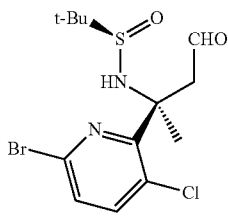 [SMILES: CC(C)(C)[S@@](=O)N[C@@](C)(CC=O)c1nc(Br)ccc1Cl]

Crude (S)-ethyl 3-(6-bromo-3-chloropyridin-2-yl)-3-((R)-1,1-dimethylethylsulfinamido)butanoate B6b (3.0 g) was reacted with diisobutylaluminum hydride in analogy to the preparation of compound B7a to give after flash chromatography (SiO₂, gradient of EtOAc in heptane, 0 to 50% EtOAc) the title compound (2.69 g, 45%) as a pale yellow oil. MS (ESI): m/z=381.1, 383.1, 385.1 [M+H]⁺.

B7c (R², R⁴=F): (R)—N-((2R,3R)-2-(6-bromo-3-fluoropyridin-2-yl)-3-fluoro-4-oxobutan-2-yl)-2-methylpropane-2-sulfinamide

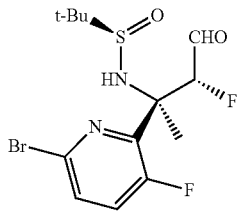 [SMILES: CC(C)(C)[S@@](=O)N[C@](C)(c1nc(Br)ccc1F)[C@@H](F)C=O]

Step 1: (R)—N-((2R,3R)-2-(6-bromo-3-fluoropyridin-2-yl)-3-fluoro-4-hydroxybutan-2-yl)-2-methylpropane-2-sulfinamide

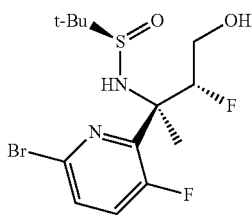 [SMILES: CC(C)(C)[S@@](=O)N[C@](C)(c1nc(Br)ccc1F)[C@@H](F)CO]

To a solution of (2R,3R)-ethyl 3-(6-bromo-3-fluoropyridin-2-yl)-3-((R)-1,1-dimethylethylsulfinamido)-2-fluorobutanoate B6c (4.13 g, 9.67 mmol) and ethanol (445 mg, 564 µl, 9.67 mmol, Eq: 1.00) in tetrahydrofuran (26.6 ml) at 0° C. was dropwise added a 2 M solution of lithium borohydride in THF (7.25 ml, 14.5 mmol) and the mixture was stirred at room temperature for 2 hours. Poured into sat NH₄Cl-sol., extracted with EtOAc, the organic layer was dried over Na₂SO₄. Removal of the solvent in vacuum give the (R)—N-((2R,3R)-2-(6-bromo-3-fluoropyridin-2-yl)-3-fluoro-4-hydroxybutan-2-yl)-2-methylpropane-2-sulfinamide (3.65 g, 9.47 mmol, 98.0% yield) as a white foam. MS (ESI): m/z=385.2, 387.2 [M+H]⁺.

Step 2: To a solution of the product from step 1 (R)—N-((2R,3R)-2-(6-bromo-3-fluoropyridin-2-yl)-3-fluoro-4-hydroxybutan-2-yl)-2-methylpropane-2-sulfinamide (3.65 g, 9.47 mmol) in dichloromethane (114 ml) at 0° C. was added Dess-Martin periodinane (4.82 g, 11.4 mmol) and the mixture was stirred at room temperature for 3 hours. Added 300 ml ether and stirred for 20 minutes, filtered off the solid and washed with ether, extracted with sat NaHCO₃-sol., the organic layer was dried over Na₂SO₄. Removal of the solvent in vacuum left a white solid, which was triturated with DCM, filtered off the solid and evaporated the organic layer totally to give 3.7 g of a yellow foam. The crude material was purified by flash chromatography (silica gel, 50 g, 0% to 70% EtOAc in heptane) to give the (R)—N-((2R,3R)-2-(6-bromo-3-fluoropyridin-2-yl)-3-fluoro-4-oxobutan-2-yl)-2-methylpropane-2-sulfinamide (2.36 g, 6.16 mmol, 65.0% yield) as a white solid. MS (ESI): m/z=383.1, 385.1 [M+H]⁺.

Synthesis of the Intermediate Trimethylsilyl Ethers B8

B8a (R²=F): (R)—N-((2S,4S)-2-(6-Bromo-3-fluoropyridin-2-yl)-5,5,5-trifluoro-4-(trimethylsilyloxy)pentan-2-yl)-2-methylpropane-2-sulfinamide

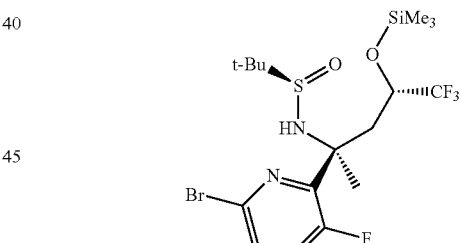

To a solution of (R)—N—((S)-2-(6-bromo-3-fluoropyridin-2-yl)-4-oxobutan-2-yl)-2-methylpropane-2-sulfinamide B7a (2.0 g) in THF (40 ml) was subsequently added at −28° C. (trifluoromethyl)trimethylsilane (1.56 g) and tetramethylammonium fluoride (51.2 mg) and stirring of the yellow solution was continued for 1 h. A further portion of tetramethylammonium fluoride (564 mg) was added and stirred was continued at −20° C. for 1 h. The mixture was partitioned between aqueous saturated NaHCO₃ (100 ml) and EtOAc (200 ml), the organic layer was washed with brine, dried, evaporated and the residue purified by flash chromatography (SiO₂, gradient of AcOEt in heptane, 17-25% EtOAc) to give an inseparable 1:1 mixture of the title compound and its deprotected alcohol (1.10 g) as a yellow oil. MS (ESI): m/z=507.3, 509.3 [M+H]⁺.

The slower eluting fraction contained the epimeric alcohol, (R)—N-((2S,4R)-2-(6-bromo-3-fluoropyridin-2-yl)-5, 5,5-trifluoro-4-hydroxypentan-2-yl)-2-methylpropane-2-sulfinamide (0.40 g) as a yellow oil. MS (ESI): m/z=435.3, 437.3 [M+H]+.

B8b (R²=Cl): (R)—N-((2S,4S)-2-(6-Bromo-3-chloropyridin-2-yl)-5,5,5-trifluoro-4-(trimethylsilyloxy)pentan-2-yl)-2-methylpropane-2-sulfinamide

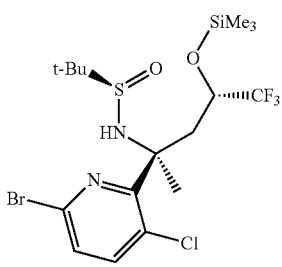 [SMILES: CC(C)(C)[S@@](=O)N[C@@](C)(C[C@H](O[Si](C)(C)C)C(F)(F)F)c1nc(Br)ccc1Cl]

(R)—N—((S)-2-(6-Bromo-3-chloropyridin-2-yl)-4-oxobutan-2-yl)-2-methylpropane-2-sulfinamide B7b (1.10 g) was reacted with (trifluoromethyl)trimethylsilane in analogy to the preparation of compound B8a to give after flash chromatography (SiO₂, gradient of EtOAc in heptane, 15 to 35% EtOAc) the faster eluting undesired epimer, (R)—N-((2S,4R)-2-(6-bromo-3-chloropyridin-2-yl)-5,5,5-trifluoro-4-(trimethylsilyloxy)pentan-2-yl)-2-methylpropane-2-sulfinamide (165 mg, 11%) as a colorless oil. MS (ESI): m/z=523.0, 525.0, 527.0 [M+H]+.

The slower eluting fraction contained the title compound (0.67 g, 44%) as a colorless oil. MS (ESI): m/z=523.0, 525.0, 527.0 [M+H]+.

B8c (R², R⁴=F): (R)—N-((2R,3R,4S)-2-(6-Bromo-3-fluoropyridin-2-yl)-3,5,5,5-tetrafluoro-4-(trimethylsilyloxy)pentan-2-yl)-2-methylpropane-2-sulfinamide and B8d (R², R⁴=F) (R)—N-((2R,3R,4R)-2-(6-Bromo-3-fluoropyridin-2-yl)-3,5,5,5-tetrafluoro-4-(trimethylsilyloxy)pentan-2-yl)-2-methylpropane-2-sulfinamide

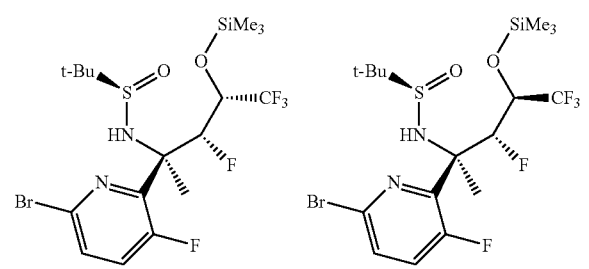 [SMILES: CC(C)(C)[S@@](=O)N[C@](C)(c1nc(Br)ccc1F)[C@@H](F)[C@H](O[Si](C)(C)C)C(F)(F)F ; CC(C)(C)[S@@](=O)N[C@](C)(c1nc(Br)ccc1F)[C@@H](F)[C@@H](O[Si](C)(C)C)C(F)(F)F]

To a solution of (R)—N-((2R,3R)-2-(6-bromo-3-fluoropyridin-2-yl)-3-fluoro-4-oxobutan-2-yl)-2-methylpropane-2-sulfinamide B7c (2.047 g, 5.34 mmol) in tetrahydrofuran (30.7 ml) at 20° C. was added (trifluoromethyl)trimethylsilane (1.52 g, 1.71 ml, 10.7 mmol, Eq: 2) followed by tetrabutylammonium fluoride (TBAF, 1 M in THF) (534 µl, 534 µmol) and the mixture was stirred at 20° C. for 2 hours. Poured into sat NH₄Cl-sol., extracted with EtOAc, the organic layer was dried over Na₂SO₄. Removal of the solvent in vacuum left a yellow oil. The crude material was purified by flash chromatography (silica gel, 20 g, 0% to 50% EtOAc in heptane) to give (R)—N-((2R,3R,4R)-2-(6-bromo-3-fluoropyridin-2-yl)-3,5,5,5-tetrafluoro-4-(trimethylsilyloxy)pentan-2-yl)-2-methylpropane-2-sulfinamide B8d (432 mg, 822 µmol, 15.4% yield) as the faster eluting isomer and (R)—N-((2R,3R,4S)-2-(6-bromo-3-fluoropyridin-2-yl)-3,5,5,5-tetrafluoro-4-(trimethylsilyloxy)pentan-2-yl)-2-methylpropane-2-sulfinamide B8c (495 mg, 942 µmol, 17.6% yield) as the slower eluting isomer. Additional (R)—N-((2R,3R,4R)-2-(6-bromo-3-fluoropyridin-2-yl)-3,5,5,5-tetrafluoro-4-hydroxypentan-2-yl)-2-methylpropane-2-sulfinamide (376 mg, 830 µmol, 15.5% yield) was also isolated.

B8c: MS (ESI): m/z=525.1, 527.1 [M+H]+; B8d: MS (ESI): m/z=525.1, 527.1 [M+H]+.

Synthesis of the Intermediate Aminoalcohols B9

B9a (R²=F): (2S,4S)-4-Amino-4-(6-bromo-3-fluoropyridin-2-yl)-1,1,1-trifluoropentan-2-ol

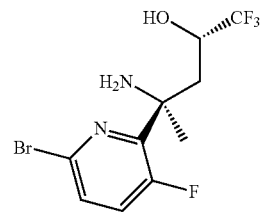 [SMILES: C[C@](N)(C[C@H](O)C(F)(F)F)c1nc(Br)ccc1F]

To a 1:1-mixture of (R)—N-((2S,4S)-2-(6-bromo-3-fluoropyridin-2-yl)-5,5,5-trifluoro-4-(trimethylsilyloxy)pentan-2-yl)-2-methylpropane-2-sulfinamide B8a and its deprotected alcohol (1.07 g) in dioxane (38 ml) was added at 22° C. hydrochloric acid (4 M in dioxane, 2.5 ml) and stirring of the solution was continued for 1 h. The mixture was evaporated, the residue partitioned between EtOAc and ice water, the pH of the aqueous layer was adjusted to 8 with aqueous saturated NaHCO₃ and extracted with EtOAc. The organic layer was dried and evaporated to give the crude title compound (0.70 g) as a pale yellow oil. MS (ESI): m/z=331.3, 333.3 [M+H]+.

B9b (R²=Cl): (2S,4S)-4-Amino-4-(6-bromo-3-chloropyridin-2-yl)-1,1,1-trifluoropentan-2-ol

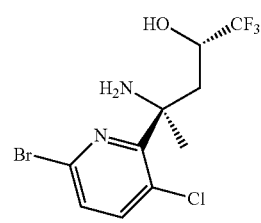 [SMILES: C[C@](N)(C[C@H](O)C(F)(F)F)c1nc(Br)ccc1Cl]

(R)—N-((2S,4S)-2-(6-Bromo-3-chloropyridin-2-yl)-5,5,5-trifluoro-4-(trimethylsilyloxy)pentan-2-yl)-2-methylpropane-2-sulfinamide B8b (0.56 g) was deprotected with hydrochloric acid in analogy to the preparation of compound B9a to give the crude title compound (345 mg, 93%) as a colorless oil. MS (ESI): m/z=347.4, 349.4, 351.4 [M+H]+.

B9c (R², R⁴=F): (2S,3R,4R)-4-Amino-4-(6-bromo-3-fluoropyridin-2-yl)-1,1,1,3-tetrafluoropentan-2-ol

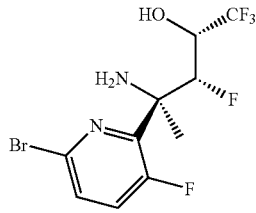 [SMILES: C[C@@](N)(c1nc(Br)ccc1F)[C@@H](F)[C@H](O)C(F)(F)F]

To a solution of (R)—N-((2R,3R,4S)-2-(6-bromo-3-fluoropyridin-2-yl)-3,5,5,5-tetrafluoro-4-(trimethylsilyloxy)pentan-2-yl)-2-methylpropane-2-sulfinamide B8c (495 mg, 942 µmol) in tetrahydrofuran (19 ml) at room temperature was added conc. HCl (495 mg, 309 µl, 3.77 mmol) and the mixture was stirred at room temperature for 2 hours. Poured into sat. NaHCO₃-sol., extracted with EtOAc, the organic layer was dried over Na₂SO₄. Removal of the solvent in vacuum left a yellow oil. The crude material was purified by flash chromatography (silica gel, 10 g, 0% to 40% EtOAc in heptane) to give the (2S,3R,4R)-4-amino-4-(6-bromo-3-fluoropyridin-2-yl)-1,1,1,3-tetrafluoropentan-2-ol (95 mg, 272 µmol, 28.9% yield) as a colorless solid. MS (ESI): m/z=349.1, 351.1 [M+H]⁺.

B9d (R², R⁴=F): (2R,3R,4R)-4-Amino-4-(6-bromo-3-fluoropyridin-2-yl)-1,1,1,3-tetrafluoropentan-2-ol

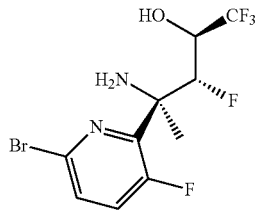 [SMILES: C[C@@](N)(c1nc(Br)ccc1F)[C@@H](F)[C@@H](O)C(F)(F)F]

To a solution of (R)—N-((2R,3R,4R)-2-(6-bromo-3-fluoropyridin-2-yl)-3,5,5,5-tetrafluoro-4-hydroxypentan-2-yl)-2-methylpropane-2-sulfinamide Bbd (680 mg, 1.5 mmol) in tetrahydrofuran (5 ml) at 0° C. was dropwise added HCl (4 M in dioxane) (375 µl, 1.5 mmol) and the mixture was stirred at room temperature for 2 hours. Poured into sat NaHCO₃-sol., extracted with EtOAc, the organic layer was dried over Na₂SO₄. Removal of the solvent in vacuum left a yellow oil. The crude material was purified by flash chromatography (silica gel, 20 g, 0% to 50% EtOAc in heptane) to give 373 mg white where the chiral auxiliary was moved to the hydroxyl group. Dissolved in MeOH (10 ml), cooled to 0° C., added excess 3 M NaOH excess and stirred for 30 minutes. Extracted with water and EtOAc, dried the organic layer over Na₂SO₄, filtered off and evaporated totally. The crude material was purified by flash chromatography (silica gel, 20 g, EtOAc in heptane, 0 to 50%) to give (2R,3R,4R)-4-amino-4-(6-bromo-3-fluoropyridin-2-yl)-1,1,1,3-tetrafluoropentan-2-ol (373 mg, 1.07 mmol, 71.2% yield) as a white solid. MS (ESI): m/z=349.1, 351.1 [M+H]⁺.

Synthesis of the Intermediate Aminooxazines B10

B10a (R²=F): (4S,6S)-4-(6-Bromo-3-fluoropyridin-2-yl)-4-methyl-6-(trifluoromethyl)-5,6-dihydro-4H-1,3-oxazin-2-amine

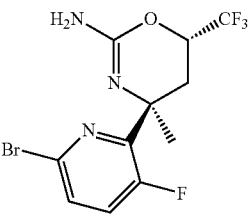 [SMILES: C[C@@]1(c2nc(Br)ccc2F)C[C@@H](C(F)(F)F)OC(N)=N1]

To a solution of (2S,4S)-4-amino-4-(6-bromo-3-fluoropyridin-2-yl)-1,1,1-trifluoropentan-2-ol B9a (670 mg) in ethanol (14 ml) was added at 22° C. a solution of Br—CN in acetonitrile (5 M, 0.61 ml) and the mixture was heated in a sealed tube to 85° C. for 15 h. The mixture was evaporated, the residue partitioned between half saturated aqueous Na₂CO₃ and EtOAc, The organic layer was dried, evaporated and the residue purified by flash chromatography (SiO₂, gradient of EtOAc in heptane, 20 to 80% EtOAc) to give the title compound (255 mg, 35%) as a pale yellow solid. MS (ESI): m/z=356.4, 358.4 [M+H]⁺.

B10b (R²=Cl): (4S,6S)-4-(6-Bromo-3-chloropyridin-2-yl)-4-methyl-6-(trifluoromethyl)-5,6-dihydro-4H-1,3-oxazin-2-amine

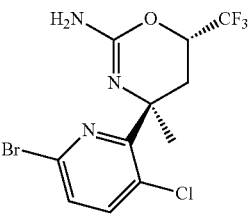 [SMILES: C[C@@]1(c2nc(Br)ccc2Cl)C[C@@H](C(F)(F)F)OC(N)=N1]

(2S,4S)-4-Amino-4-(6-bromo-3-chloropyridin-2-yl)-1,1,1-trifluoropentan-2-ol B9b (335 mg) was reacted with Br—CN in analogy to the preparation of compound B10a to give the title compound (148 mg, 41%) as a pale yellow oil. MS (ESI): m/z=372.0, 374.0, 376.0 [M+H]⁺.

Synthesis of the Intermediate Boc-Aminooxazines B11

B11a (R²=F): tert-Butyl (4S,6S)-4-(6-bromo-3-fluoropyridin-2-yl)-4-methyl-6-(trifluoromethyl)-5,6-dihydro-4H-1,3-oxazin-2-ylcarbamate

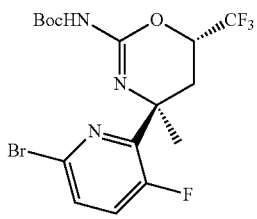 [SMILES: CC(C)(C)OC(=O)NC1=N[C@](C)(c2nc(Br)ccc2F)C[C@@H](C(F)(F)F)O1]

To a solution of (4S,6S)-4-(6-bromo-3-fluoropyridin-2-yl)-4-methyl-6-(trifluoromethyl)-5,6-dihydro-4H-1,3-oxazin-2-amine B10a (245 mg) in dichloromethane (5 ml) was subsequently added at 22° C. N,N-diisopropylethylamine (124 mg) and Boc-anhydride (180 mg) and stirring was continued for 15 h. The mixture was evaporated and the residue purified by flash chromatography (SiO₂, gradient of EtOAc in heptane, 5 to 100% EtOAc) to give the title compound (276 mg, 88%) as a colorless solid. MS (ESI): m/z=456.3, 458.3 [M+H]⁺.

B11b (R²═Cl): tert-Butyl (4S,6S)-4-(6-bromo-3-chloropyridin-2-yl)-4-methyl-6-(trifluoromethyl)-5,6-dihydro-4H-1,3-oxazin-2-ylcarbamate

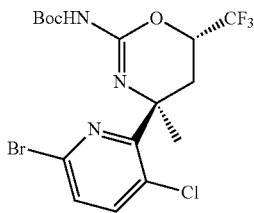

(4S,6S)-4-(6-Bromo-3-chloropyridin-2-yl)-4-methyl-6-(trifluoromethyl)-5,6-dihydro-4H-1,3-oxazin-2-amine B10b (27 mg) was reacted with Boc-anhydride in analogy to the preparation of compound B11a to give after flash chromatography (SiO₂, gradient of EtOAc in heptane, 0 to 20% EtOAc) the title compound (27 mg, 79%) as a white solid. MS (ESI): m/z=472.2, 474.2, 476.2 [M+H]⁺.

B11c (R², R⁴═F): tert-Butyl (4R,5R,6S)-4-(6-bromo-3-fluoropyridin-2-yl)-5-fluoro-4-methyl-6-(trifluoromethyl)-5,6-dihydro-4H-1,3-oxazin-2-ylcarbamate

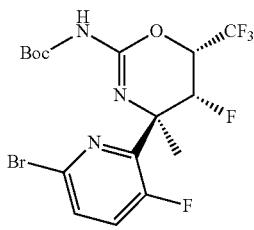 [SMILES: CC(C)(C)OC(=O)NC1=N[C@](C)(c2nc(Br)ccc2F)[C@@H](F)[C@@H](C(F)(F)F)O1]

Step 1: N-((2R,3R,4S)-2-(6-Bromo-3-fluoropyridin-2-yl)-3,5,5,5-tetrafluoro-4-hydroxypentan-2-ylcarbamothioyl)benzamide

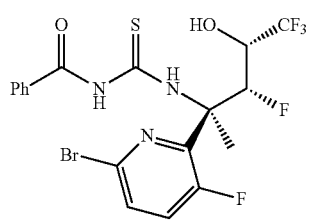 [SMILES: C[C@@](NC(=S)NC(=O)c1ccccc1)(c1nc(Br)ccc1F)[C@@H](F)[C@H](O)C(F)(F)F]

To a solution of (2S,3R,4R)-4-amino-4-(6-bromo-3-fluoropyridin-2-yl)-1,1,1,3-tetrafluoropentan-2-ol B9c (145 mg, 415 µmol) in tetrahydrofuran (14 ml) at room temperature was added benzoyl isothiocyanate (67.8 mg, 55.9 µl, 415 µmol) and the mixture was stirred at room temperature for 16 hours. All volatiles were removed in vacuum and the crude material was purified by flash chromatography (silica gel, 10 g, 0% to 40% EtOAc in heptane) to give the N-((2R,3R,4S)-2-(6-bromo-3-fluoropyridin-2-yl)-3,5,5,5-tetrafluoro-4-hydroxypentan-2-ylcarbamothioyl)benzamide (203 mg, 396 µmol, 95.4% yield) as a light yellow foam. MS (ESI): m/z=512.1, 514.1 [M+H]⁺.

Step 2: N-((4R,5R,6S)-4-(6-Bromo-3-fluoropyridin-2-yl)-5-fluoro-4-methyl-6-(trifluoromethyl)-5,6-dihydro-4H-1,3-oxazin-2-yl)benzamide

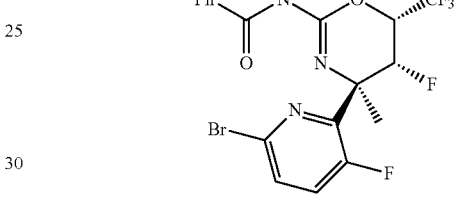

To a solution of N-((2R,3R,4S)-2-(6-bromo-3-fluoropyridin-2-yl)-3,5,5,5-tetrafluoro-4-hydroxypentan-2-ylcarbamothioyl)benzamide (from step 1 above) (203 mg, 396 µmol) in acetonitrile (4 ml) at room temperature was added EDC.HCl (114 mg, 594 µmol) and the mixture was stirred at 80° C. for 2 hours. The crude material was purified by flash chromatography (silica gel, 20 g, 0% to 30% EtOAc in heptane) to give the N-((4R,5R,6S)-4-(6-bromo-3-fluoropyridin-2-yl)-5-fluoro-4-methyl-6-(trifluoromethyl)-5,6-dihydro-4H-1,3-oxazin-2-yl)benzamide (157 mg, 328 µmol, 82.9% yield) as a white foam. MS (ESI): m/z=478.2, 480.2 [M+H]⁺.

Step 3: tert-Butyl benzoyl((4R,5R,6S)-4-(6-bromo-3-fluoropyridin-2-yl)-5-fluoro-4-methyl-6-(trifluoromethyl)-5,6-dihydro-4H-1,3-oxazin-2-yl)carbamate

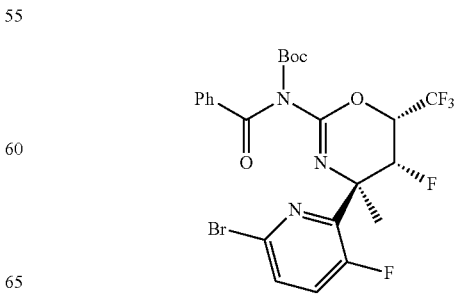

To a solution of N-((4R,5R,6S)-4-(6-bromo-3-fluoropyridin-2-yl)-5-fluoro-4-methyl-6-(trifluoromethyl)-5,6-dihydro-4H-1,3-oxazin-2-yl)benzamide (from step 2 above) (157 mg, 328 µmol) in tetrahydrofuran (15.4 ml) at room temperature was added di-tert-butyl dicarbonate (Boc₂O) (78.8 mg, 83.8 µl, 361 µmol) and triethylamine (36.5 mg, 50.3 µl, 361 µmol) followed by 4-dimethylaminopyridine (8.02 mg, 65.7 µmol) and the mixture was stirred at room temperature for 30 minutes. Removal of the solvent in vacuum at ambient temperature left a light yellow oil. The crude material was purified by flash chromatography (silica gel, 20 g, 0% to 35% EtOAc in heptane) to give the tert-butyl benzoyl((4R,5R,6S)-4-(6-bromo-3-fluoropyridin-2-yl)-5-fluoro-4-methyl-6-(trifluoromethyl)-5,6-dihydro-4H-1,3-oxazin-2-yl)carbamate (129 mg, 223 µmol, 67.9% yield) as a white foam. MS (ESI): m/z=578.2, 580.2 [M+H]⁺.

Step 4: tert-Butyl (4R,5R,6S)-4-(6-bromo-3-fluoropyridin-2-yl)-5-fluoro-4-methyl-6-(trifluoromethyl)-5,6-dihydro-4H-1,3-oxazin-2-ylcarbamate

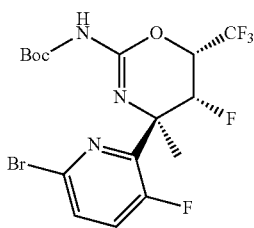 [SMILES: CC(C)(C)OC(=O)NC1=N[C@](C)(c2nc(Br)ccc2F)[C@@H](F)[C@@H](C(F)(F)F)O1]

To a solution of tert-butyl benzoyl((4R,5R,6S)-4-(6-bromo-3-fluoropyridin-2-yl)-5-fluoro-4-methyl-6-(trifluoromethyl)-5,6-dihydro-4H-1,3-oxazin-2-yl)carbamate (from step 3 above) (129 mg, 223 µmol) in methanol (10 ml) at 0° C. was added 7 M ammonia in MeOH (3.19 ml, 22.3 mmol) and the mixture was stirred at room temperature for 30 minutes. Removal of the solvent in vacuum at ambient temperature left a yellow oil. The crude material was purified by flash chromatography (silica gel, 20 g, 0% to 60% EtOAc in heptane) to give the tert-butyl (4R,5R,6S)-4-(6-bromo-3-fluoropyridin-2-yl)-5-fluoro-4-methyl-6-(trifluoromethyl)-5,6-dihydro-4H-1,3-oxazin-2-ylcarbamate (75 mg, 158 µmol, 70.9% yield) as a white solid. MS (ESI): m/z=474.1, 476.1 [M+H]⁺.

B11d (R², R⁴=F): tert-Butyl (4R,5R,6R)-4-(6-bromo-3-fluoropyridin-2-yl)-5-fluoro-4-methyl-6-(trifluoromethyl)-5,6-dihydro-4H-1,3-oxazin-2-ylcarbamate

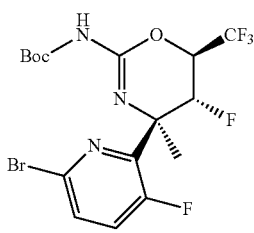 [SMILES: CC(C)(C)OC(=O)NC1=N[C@](C)(c2nc(Br)ccc2F)[C@@H](F)[C@H](C(F)(F)F)O1]

Step 1: N-((2R,3R,4R)-2-(6-Bromo-3-fluoropyridin-2-yl)-3,5,5,5-tetrafluoro-4-hydroxypentan-2-ylcarbamothioyl)benzamide

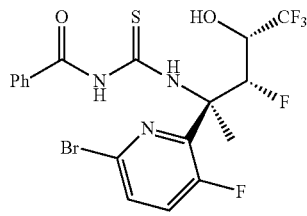 [SMILES: C[C@@](NC(=S)NC(=O)c1ccccc1)(c1nc(Br)ccc1F)[C@@H](F)[C@H](O)C(F)(F)F]

To a solution of (2S,3R,4R)-4-amino-4-(6-bromo-3-fluoropyridin-2-yl)-1,1,1,3-tetrafluoropentan-2-ol B9d (373 mg, 1.07 mmol) in tetrahydrofuran (35 ml) at room temperature was added benzoyl isothiocyanate (174 mg, 144 µl, 1.07 mmol) and the mixture was stirred at room temperature for 16 hours. All volatiles were removed in vacuum and the crude material was purified by flash chromatography (silica gel, 20 g, 0% to 40% EtOAc in heptane) to give the N-((2R,3R,4R)-2-(6-bromo-3-fluoropyridin-2-yl)-3,5,5,5-tetrafluoro-4-hydroxypentan-2-ylcarbamothioyl)benzamide (473 mg, 923 µmol, 86.4% yield) as a light yellow foam. MS (ESI): m/z=512.1, 514.1 [M+H]⁺.

Step 2: N-((4R,5R,6R)-4-(6-Bromo-3-fluoropyridin-2-yl)-5-fluoro-4-methyl-6-(trifluoromethyl)-5,6-dihydro-4H-1,3-oxazin-2-yl)benzamide

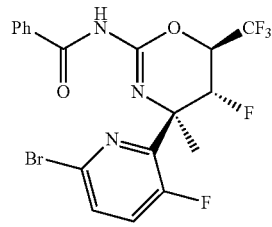 [SMILES: C[C@]1(c2nc(Br)ccc2F)N=C(NC(=O)c2ccccc2)O[C@@H](C(F)(F)F)[C@@H]1F]

To a solution of N-((2R,3R,4 S)-2-(6-bromo-3-fluoropyridin-2-yl)-3,5,5,5-tetrafluoro-4-hydroxypentan-2-ylcarbamothioyl)benzamide (from step 1 above) (473 mg, 923 µmol) in acetonitrile (10 ml) at room temperature was added EDC.HCl (265 mg, 1.38 mmol) and the mixture was stirred at 80° C. for 2 hours. The crude material was purified by flash chromatography (silica gel, 20 g, 0% to 30% EtOAc in heptane) to give the N-((4R,5R,6R)-4-(6-bromo-3-fluoropyridin-2-yl)-5-fluoro-4-methyl-6-(trifluoromethyl)-5,6-dihydro-4H-1,3-oxazin-2-yl)benzamide (330 mg, 690 µmol, 74.7% yield) as a white foam. MS (ESI): m/z=478.2, 480.2 [M+H]⁺.

Step 3: tert-Butyl benzoyl((4R,5R,6R)-4-(6-bromo-3-fluoropyridin-2-yl)-5-fluoro-4-methyl-6-(trifluoromethyl)-5,6-dihydro-4H-1,3-oxazin-2-yl)carbamate

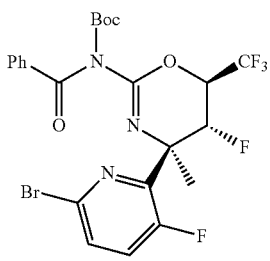 [SMILES: CC(C)(C)OC(=O)N(C(=O)c1ccccc1)C1=N[C@](C)(c2nc(Br)ccc2F)[C@@H](F)[C@H](C(F)(F)F)O1]

To a solution of N-((4R,5R,6R)-4-(6-bromo-3-fluoropyridin-2-yl)-5-fluoro-4-methyl-6-(trifluoromethyl)-5,6-dihydro-4H-1,3-oxazin-2-yl)benzamide (from step 2 above) (330 mg, 690 μmol) in tetrahydrofuran (32.4 ml) at room temperature was added di-tert-butyl dicarbonate (Boc$_2$O) (166 mg, 176 μl, 759 μmol) and triethylamine (76.8 mg, 106 μl, 759 μmol) followed by 4-dimethylaminopyridine (16.9 mg, 138 μmol) and the mixture was stirred at room temperature for 3 days. Removal of the solvent in vacuum at ambient temperature left a light yellow oil. The crude material was purified by flash chromatography (silica gel, 20 g, 0% to 35% EtOAc in heptane) to give the tert-butyl benzoyl((4R,5R,6S)-4-(6-bromo-3-fluoropyridin-2-yl)-5-fluoro-4-methyl-6-(trifluoromethyl)-5,6-dihydro-4H-1,3-oxazin-2-yl)carbamate (399 mg, 690 μmol, 100% yield) as a white foam. MS (ESI): m/z=578.2, 580.2 [M+H]$^+$.

Step 4: tert-Butyl (4R,5R,6S)-4-(6-bromo-3-fluoropyridin-2-yl)-5-fluoro-4-methyl-6-(trifluoromethyl)-5,6-dihydro-4H-1,3-oxazin-2-ylcarbamate

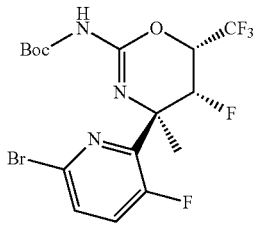 [SMILES: CC(C)(C)OC(=O)NC1=N[C@](C)(c2nc(Br)ccc2F)[C@@H](F)[C@@H](C(F)(F)F)O1]

To a solution of tert-butyl benzoyl((4R,5R,6R)-4-(6-bromo-3-fluoropyridin-2-yl)-5-fluoro-4-methyl-6-(trifluoromethyl)-5,6-dihydro-4H-1,3-oxazin-2-yl)carbamate (from step 3 above) (399 mg, 690 mot) in methanol (20 ml) at 0° C. was added 7 M ammonia in MeOH (9.86 ml, 69.0 mmol) and the mixture was stirred at room temperature for 30 minutes. Removal of the solvent in vacuum at ambient temperature left a yellow oil. The crude material was purified by flash chromatography (silica gel, 20 g, 0% to 60% EtOAc in heptane) to give the tert-butyl (4R,5R,6R)-4-(6-bromo-3-fluoropyridin-2-yl)-5-fluoro-4-methyl-6-(trifluoromethyl)-5,6-dihydro-4H-1,3-oxazin-2-ylcarbamate (237 mg, 500 μmol, 72.4% yield) as a colorless oil. MS (ESI): m/z=474.1, 476.1 [M+H]$^+$.

Synthesis of the Intermediate Boc-Aminopyridine B12

B12a (R$^2$=F): tert-Butyl (4S,6S)-4-(6-amino-3-fluoropyridin-2-yl)-4-methyl-6-(trifluoromethyl)-5,6-dihydro-4H-1,3-oxazin-2-ylcarbamate

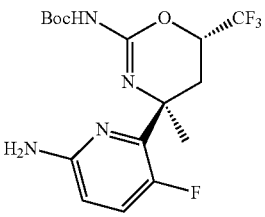 [SMILES: CC(C)(C)OC(=O)NC1=N[C@](C)(c2nc(N)ccc2F)C[C@@H](C(F)(F)F)O1]

To a solution of tert-butyl (4S,6S)-4-(6-bromo-3-fluoropyridin-2-yl)-4-methyl-6-(trifluoromethyl)-5,6-dihydro-4H-1,3-oxazin-2-ylcarbamate B11a (175 mg) in ethanol (5.4 ml) and water (2.4 ml) was subsequently added at 23° C. sodium azide (199 mg), copper (I) iodide (29 mg), sodium L-ascorbate (15.2 mg) and trans-N,N'-dimethylcyclohexane-1,2-diamine (33 mg) and stirring of the light blue solution was continued at 70° C. for 1 h. The mixture was partitioned between saturated aqueous NaHCO$_3$ and EtOAc, the organic layer was dried, evaporated and the residue purified by flash chromatography (SiO$_2$, gradient of EtOAc in heptane, 25 to 40% EtOAc) to give the title compound (82 mg, 54%) as a colorless solid. MS (ESI): m/z=393.5 [M+H]$^+$.

B12b (R$^2$=Cl): tert-Butyl (4S,6S)-4-(6-amino-3-chloropyridin-2-yl)-4-methyl-6-(trifluoromethyl)-5,6-dihydro-4H-1,3-oxazin-2-ylcarbamate

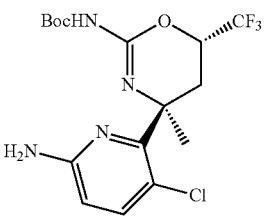 [SMILES: CC(C)(C)OC(=O)NC1=N[C@](C)(c2nc(N)ccc2Cl)C[C@@H](C(F)(F)F)O1]

tert-Butyl (4S,6S)-4-(6-Bromo-3-chloropyridin-2-yl)-4-methyl-6-(trifluoromethyl)-5,6-dihydro-4H-1,3-oxazin-2-ylcarbamate B11b (25 mg) was reacted with sodium azide in analogy to the preparation of compound B12a to give after flash chromatography (SiO$_2$, gradient of AcOEt in heptane, 10-50% EtOAc) the title compound (9 mg, 42%) as a colorless foam. MS (ESI): m/z=409.2, 411.2 [M+H]$^+$.

B12c (R², R⁴=F): tert-Butyl (4R,5R,6S)-4-(6-amino-3-fluoropyridin-2-yl)-5-fluoro-4-methyl-6-(trifluoromethyl)-5,6-dihydro-4H-1,3-oxazin-2-yl-carbamate

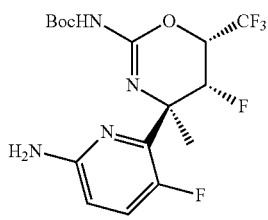 [SMILES: CC(C)(C)OC(=O)NC1=N[C@](C)(c2nc(N)ccc2F)[C@@H](F)[C@@H](C(F)(F)F)O1]

To a solution of tert-butyl (4R,5R,6S)-4-(6-bromo-3-fluoropyridin-2-yl)-5-fluoro-4-methyl-6-(trifluoromethyl)-5,6-dihydro-4H-1,3-oxazin-2-ylcarbamate B11c (75 mg, 158 μmol) in dioxane (3.00 ml) and water (1.00 ml) at room temperature was added sodium azide (82.3 mg, 1.27 mmol), sodium L-ascorbate (6.27 mg, 31.6 μmol), trans-N,N'-dimethylcyclohexane-1,2-diamine (13.5 mg, 15.0 μl, 94.9 μmol) and copper (I) iodide (12.0 mg, 63.3 μmol) after 10 minutes is was dark green-blue, the mixture was stirred at 70° C. for 30 minutes. Added again sodium L-ascorbate (6.27 mg, 31.6 μmol), trans-N,N'-dimethylcyclohexane-1,2-diamine (13.5 mg, 15.0 μl, 94.9 μmol) and copper (I) iodide (12.0 mg, 63.3 μmol) and continued stirring at 70° C. for another 30 minutes. Poured into sat. NaHCO₃-sol., extracted with EtOAc, the organic layer was dried over Na₂SO₄. Removal of the solvent in vacuum left a dark green oil. The crude material was purified by flash chromatography (silica gel, 10 g, 0% to 40% EtOAc in heptane) to give the tert-butyl (4R,5R,6S)-4-(6-amino-3-fluoropyridin-2-yl)-5-fluoro-4-methyl-6-(trifluoromethyl)-5,6-dihydro-4H-1,3-oxazin-2-ylcarbamate (29 mg, 70.7 μmol, 44.7% yield) as a white solid. MS (ESI): m/z=411.2 [M+H]⁺.

B12d (R², R⁴=F): tert-Butyl (4R,5R,6R)-4-(6-amino-3-fluoropyridin-2-yl)-5-fluoro-4-methyl-6-(trifluoromethyl)-5,6-dihydro-4H-1,3-oxazin-2-yl-carbamate

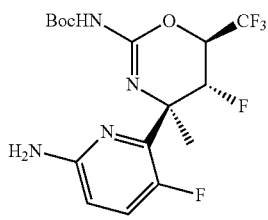 [SMILES: CC(C)(C)OC(=O)NC1=N[C@](C)(c2nc(N)ccc2F)[C@@H](F)[C@H](C(F)(F)F)O1]

To a solution of tert-butyl (4R,5R,6R)-4-(6-bromo-3-fluoropyridin-2-yl)-5-fluoro-4-methyl-6-(trifluoromethyl)-5,6-dihydro-4H-1,3-oxazin-2-ylcarbamate B11d (237 mg, 500 μmol) in dioxane (3.00 ml) and water (1.00 ml) at room temperature was added sodium azide (260 mg, 4.00 mmol), sodium L-ascorbate (19.8 mg, 100 μmol), trans-N,N'-dimethylcyclohexane-1,2-diamine (42.7 mg, 47.3 μl, 300 μmol) and copper (I) iodide (38.1 mg, 200 μmol) after 10 minutes is was dark green-blue, the mixture was stirred at 70° C. for 1 hour. Added again sodium L-ascorbate (19.8 mg, 100 μmol), trans-N,N'-dimethylcyclohexane-1,2-diamine (42.7 mg, 47.3 μl, 300 μmol) and copper (I) iodide (38.1 mg, 200 μmol) and continued stirring at 70° C. for another 30 minutes. Poured into sat. NaHCO₃-sol., extracted with EtOAc, the organic layer was dried over Na₂SO₄. Removal of the solvent in vacuum left a dark green oil. The crude material was purified by flash chromatography (silica gel, 10 g, 0% to 40% EtOAc in heptane) to give the tert-butyl (4R,5R,6R)-4-(6-amino-3-fluoropyridin-2-yl)-5-fluoro-4-methyl-6-(trifluoromethyl)-5,6-dihydro-4H-1,3-oxazin-2-ylcarbamate (50 mg, 122 μmol, 24.4% yield) as a white solid. MS (ESI): m/z=411.2 [M+H]⁺.

Synthesis of the Intermediate Boc-Amides A15 and B13 and Deprotected Amides I

General Procedure for the Coupling of the Boc-Aminopyridines A14 or B12 with the Acid to the Boc-Amide A15 or B13

T3P-Method:

To a solution of the Boc-aminopyridine A14 or B12 (0.10 mmol) and the acid (0.2 mmol) in EtOAc (1.2 ml) was added at 22° C. T3P (50% in EtOAc, 0.09 ml, 0.15 mmol) and stirring was continued 2 h. A further portion of T3P (0.05 ml, 0.08 mmol) was added and stirring was continued for 2 h. The mixture was partitioned between saturated aqueous NaHCO₃ and EtOAc, the organic layer was dried, evaporated and the residue purified by flash chromatography (SiO₂, gradient of EtOAc in heptane) to give the Boc-amide A15 or B13.

Ghosez's Reagent Method:

To a suspension of the acid (197 μmol, Eq: 1.5) in dry dichloromethane (1.5 ml) at 0° C. was dropwise added 1-chloro-N,N,2-trimethylpropenylamine (Ghosez's reagent) (52.8 mg, 395 μmol, Eq: 3) and the mixture was stirred at 0° C. for 1 hour. This mixture was then added to a solution of the Boc-aminopyridine A14 or B12 (132 μmol, Eq: 1.00) and diisopropylethylamine (51.0 mg, 69.0 μl, 395 μmol, Eq: 3) in dry dichloromethane (1.5 ml) at 0° C. The ice bath was removed and the mixture was stirred 1 to 16 hour(s) at ambient temperature. Evaporated totally at ambient temperature and directly purified by flash chromatography (silica gel, gradient of EtOAc in heptane) to give the Boc-amide A15 or B13.

General Procedure for the Deprotection of the Boc-Amide A15 or B13 to the Amide I To a solution of the Boc-amide A15 or B13 (0.04 mmol) in dichloromethane (0.5 ml) was added at 22° C. trifluoroacetic acid (1.2 mmol) and stirring was continued for 16 h. The mixture was evaporated, the residue diluted with EtOAc and evaporated again. The residue was triturated with diethyl ether/pentane, the suspension was filtered and the residue dried to give the amide I. Alternative workup to obtain the free base: after stirring for 16 h, all volatiles were removed in vacuum, the residue was partitioned between EtOAc and sat. NaHCO₃-sol., the organic layer was washed with brine and dried over Na₂SO₄. Filtration and removal of the solvent in vacuum left the crude product which was purified by flash chromatography to give the amide I.

B13a-1 (R²=F): tert-Butyl (4S,6S)-4-(6-(3-chloro-5-cyanopicolinamido)-3-fluoropyridin-2-yl)-4-methyl-6-(trifluoromethyl)-5,6-dihydro-4H-1,3-oxazin-2-ylcarbamate

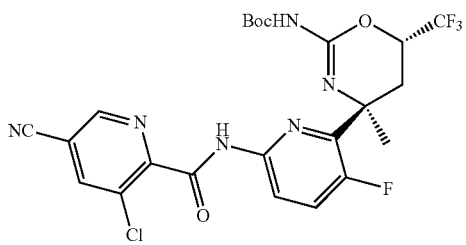 [SMILES: CC(C)(C)OC(=O)NC1=N[C@](C)(c2nc(NC(=O)c3ncc(C#N)cc3Cl)ccc2F)C[C@@H](C(F)(F)F)O1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 3-chloro-5-cyano-pyridine-2-carboxylic acid according to the T3P-method to give after flash chromatography (SiO₂, gradient of EtOAc in heptane, 5 to 50% EtOAc) the title compound (17 mg, 30%) as a colorless solid. MS (ESI): m/z=557.6, 559.6 [M+H]⁺.

B13a-2 (R²=F): tert-Butyl (4S,6S)-4-(6-(3-chloro-5-(trifluoromethyl)picolinamido)-3-fluoropyridin-2-yl)-4-methyl-6-(trifluoromethyl)-5,6-dihydro-4H-1,3-oxazin-2-ylcarbamate

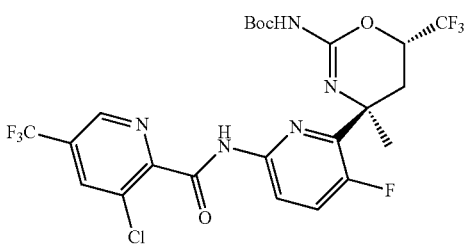

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 3-chloro-5-(trifluoromethyl)pyridine-2-carboxylic acid according to the T3P-method to give after flash chromatography (SiO₂, gradient of EtOAc in heptane, 5 to 50% EtOAc) the title compound (26 mg, 44%) as a colorless solid. MS (ESI): m/z=600.3, 602.3 [M+H]⁺.

B13a-3 (R²=F): tert-Butyl (4S,6S)-4-(3-fluoro-6-(5-methoxypyrazine-2-carboxamido)pyridin-2-yl)-4-methyl-6-(trifluoromethyl)-5,6-dihydro-4H-1,3-oxazin-2-ylcarbamate

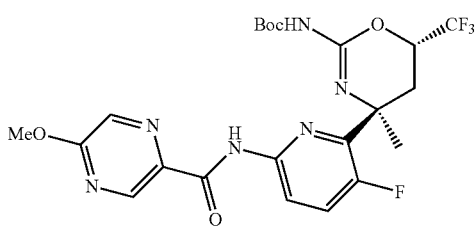 [SMILES: COc1cnc(C(=O)Nc2ccc(F)c([C@]3(C)C[C@@H](C(F)(F)F)OC(NC(=O)OC(C)(C)C)=N3)n2)cn1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 5-methoxy-pyrazine-2-carboxylic acid according to the T3P-method to give after flash chromatography (SiO₂, gradient of AcOEt in heptane, 5-50% EtOAc) the title compound (14 mg, 27%) as an off-white solid. MS (ESI): m/z=529.4 [M+H]⁺.

B13a-4 (R²=F): tert-Butyl (4S,6S)-4-(6-(5-cyano-3-methylpicolinamido)-3-fluoropyridin-2-yl)-4-methyl-6-(trifluoromethyl)-5,6-dihydro-4H-1,3-oxazin-2-ylcarbamate

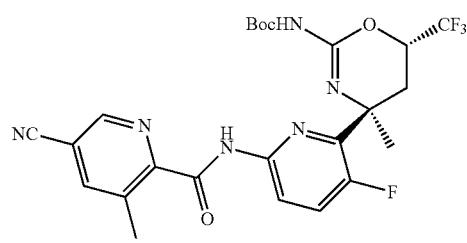 [SMILES: Cc1cc(C#N)cnc1C(=O)Nc1ccc(F)c([C@]2(C)C[C@@H](C(F)(F)F)OC(NC(=O)OC(C)(C)C)=N2)n1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 5-cyano-3-methyl-pyridine-2-carboxylic acid according to the T3P-method to give after flash chromatography (SiO₂, gradient of EtOAc in heptane, 5 to 50% EtOAc) the title compound (22 mg, 41%) as a colorless foam. MS (ESI): m/z=537.6 [M+H]⁺.

B13a-5 (R²=F): tert-Butyl (4S,6S)-4-(3-fluoro-6-(5-methoxypicolinamido)pyridin-2-yl)-4-methyl-6-(trifluoromethyl)-5,6-dihydro-4H-1,3-oxazin-2-ylcarbamate

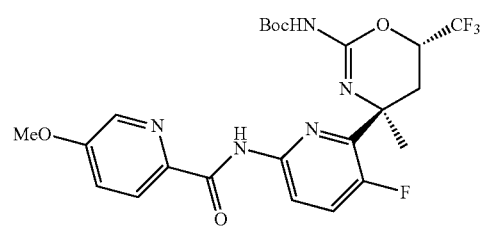 [SMILES: COc1ccc(C(=O)Nc2ccc(F)c([C@]3(C)C[C@@H](C(F)(F)F)OC(NC(=O)OC(C)(C)C)=N3)n2)nc1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 5-methoxy-pyridine-2-carboxylic acid according to the T3P-method to give after flash chromatography (SiO₂, gradient of EtOAc in heptane, 5 to 50% EtOAc) the title compound (16 mg, 30%) as a colorless foam. MS (ESI): m/z=528.6 [M+H]⁺.

B13a-6 (R²═F): tert-Butyl (4S,6S)-4-(6-(4-chloro-1-(difluoromethyl)-1H-pyrazole-3-carboxamido)-3-fluoropyridin-2-yl)-4-methyl-6-(trifluoromethyl)-5,6-dihydro-4H-1,3-oxazin-2-ylcarbamate

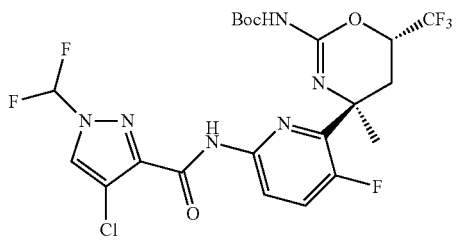 [SMILES: CC(C)(C)OC(=O)NC1=N[C@](C)(c2nc(NC(=O)c3nn(C(F)F)cc3Cl)ccc2F)C[C@@H](C(F)(F)F)O1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 4-chloro-1-(difluoromethyl)pyrazole-3-carboxylic acid, prepared according to H. Hilpert et al., *J. Med. Chem.* 2013, 56, 3980, according to the T3P-method to give after flash chromatography (SiO₂, gradient of EtOAc in heptane, 5 to 50% EtOAc) the title compound (26 mg, 46%) as an off-white solid. MS (ESI): m/z=571.5, 573.5 [M+H]⁺.

B13a-7 (R²═F): tert-Butyl (4S,6S)-4-(6-(5-(difluoromethyl)pyrazine-2-carboxamido)-3-fluoropyridin-2-yl)-4-methyl-6-(trifluoromethyl)-5,6-dihydro-4H-1,3-oxazin-2-ylcarbamate

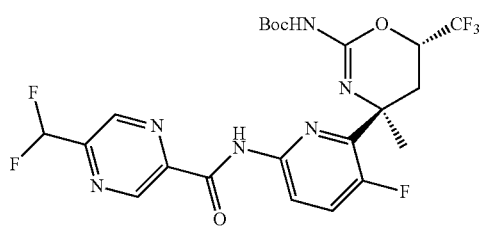 [SMILES: CC(C)(C)OC(=O)NC1=N[C@](C)(c2nc(NC(=O)c3cnc(C(F)F)cn3)ccc2F)C[C@@H](C(F)(F)F)O1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 5-(difluoromethyl)pyrazine-2-carboxylic acid, prepared according to WO2009091016, according to the T3P-method to give after flash chromatography (SiO₂, gradient of EtOAc in heptane, 5 to 50% EtOAc) the title compound (30 mg, 55%) as an colorless foam. MS (ESI): m/z=549.2 [M+H]⁺.

B13a-8 (R²═F): tert-Butyl (4S,6S)-4-(6-(3,5-dichloropicolinamido)-3-fluoropyridin-2-yl)-4-methyl-6-(trifluoromethyl)-5,6-dihydro-4H-1,3-oxazin-2-ylcarbamate

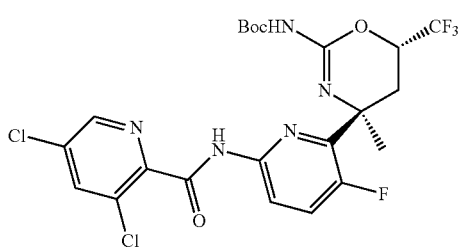 [SMILES: CC(C)(C)OC(=O)NC1=N[C@](C)(c2nc(NC(=O)c3ncc(Cl)cc3Cl)ccc2F)C[C@@H](C(F)(F)F)O1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 3,5-dichloropyridine-2-carboxylic acid according to the T3P-method to give after flash chromatography (SiO₂, gradient of EtOAc in heptane, 5 to 50% EtOAc) the title compound (26 mg, 46%) as an colorless solid. MS (ESI): m/z=566.5, 568.5 [M+H]⁺.

B13a-9 (R²═F): tert-Butyl (4S,6S)-4-(3-fluoro-6-(5-(fluoromethoxy)picolinamido)pyridin-2-yl)-4-methyl-6-(trifluoromethyl)-5,6-dihydro-4H-1,3-oxazin-2-ylcarbamate

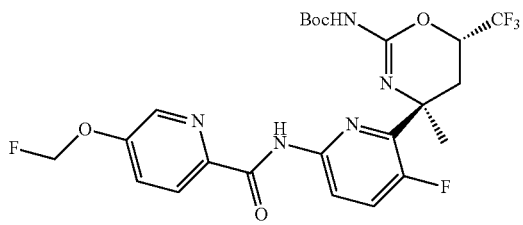 [SMILES: CC(C)(C)OC(=O)NC1=N[C@](C)(c2nc(NC(=O)c3ccc(OCF)cn3)ccc2F)C[C@@H](C(F)(F)F)O1]

tert-Butyl (4S,6S)-4-(6-amino-3-fluoropyridin-2-yl)-4-methyl-6-(trifluoromethyl)-5,6-dihydro-4H-1,3-oxazin-2-ylcarbamate B12a (39 mg) was coupled with 5-(fluoromethoxy)pyridine-2-carboxylic acid, prepared according to WO 2009091016, according to the T3P-method to give after flash chromatography (SiO₂, gradient of EtOAc in heptane, 5 to 60% EtOAc) the title compound (18 mg, 33%) as an colorless solid. MS (ESI): m/z=546.5 [M+H]⁺.

B13b (R²═Cl): tert-Butyl (4S,6S)-4-(3-chloro-6-(5-cyanopicolinamido)pyridin-2-yl)-4-methyl-6-(trifluoromethyl)-5,6-dihydro-4H-1,3-oxazin-2-ylcarbamate

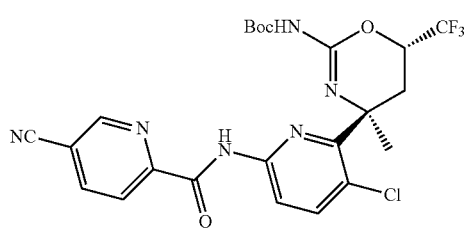 [SMILES: CC(C)(C)OC(=O)NC1=N[C@](C)(c2nc(NC(=O)c3ccc(C#N)cn3)ccc2Cl)C[C@@H](C(F)(F)F)O1]

To a solution of 5-cyanopyridine-2-carboxylic acid (14 mg) in dichloromethane (0.6 ml) and dimethylformamide (0.3 ml) was added subsequently at 22° C. N,N-diisopropylethylamine (29 mg) and HATU (42 mg) and after 15 min tert-butyl (4S,6S)-4-(6-amino-3-chloropyridin-2-yl)-4-methyl-6-(trifluoromethyl)-5,6-dihydro-4H-1,3-oxazin-2-ylcarbamate B12b (30 mg) and stirring was continued for 4 h. The mixture was partitioned between saturated aqueous NaHCO₃ and dichloromethane, the organic layer was dried, evaporated and the residue purified by flash chromatography (SiO₂, gradient of EtOAc in heptane, 5 to 50% EtOAc) to give the title compound (4 mg, 10%) as a white solid. MS (ESI): m/z=539.2, 541.2 [M+H]⁺.

B13c-1 (R², R⁴=F): tert-Butyl (4R,5R,6S)-4-(6-(5-cyanopicolinamido)-3-fluoropyridin-2-yl)-5-fluoro-4-methyl-6-(trifluoromethyl)-5,6-dihydro-4H-1,3-oxazin-2-ylcarbamate

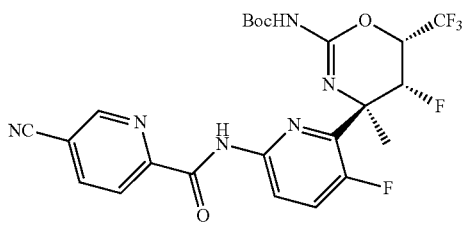 [SMILES: CC(C)(C)OC(=O)NC1=N[C@](C)(c2nc(NC(=O)c3ccc(C#N)cn3)ccc2F)[C@@H](F)[C@@H](C(F)(F)F)O1]

tert-Butyl (4R,5R,6S)-4-(6-amino-3-fluoropyridin-2-yl)-5-fluoro-4-methyl-6-(trifluoromethyl)-5,6-dihydro-4H-1,3-oxazin-2-ylcarbamate B12c (29 mg, 70.7 μmol) was coupled with 5-cyanopicolinic acid according to the Ghosez's reagent-method to give after flash chromatography (SiO₂, gradient of EtOAc in heptane, 0 to 45% EtOAc) the title compound (23 mg, 42.6 μmol, 60.2% yield) as a white foam. MS (ESI): m/z=541.3 [M+H]⁺.

B13d-1 (R², R⁴=F): tert-Butyl (4R,5R,6R)-4-(6-(5-cyanopicolinamido)-3-fluoropyridin-2-yl)-5-fluoro-4-methyl-6-(trifluoromethyl)-5,6-dihydro-4H-1,3-oxazin-2-ylcarbamate

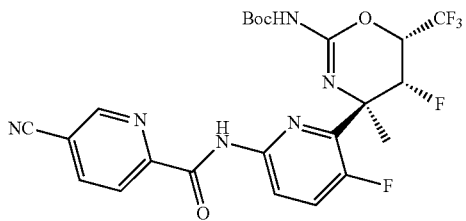 [SMILES: CC(C)(C)OC(=O)NC1=N[C@](C)(c2nc(NC(=O)c3ccc(C#N)cn3)ccc2F)[C@@H](F)[C@@H](C(F)(F)F)O1]

tert-Butyl (4R,5R,6R)-4-(6-amino-3-fluoropyridin-2-yl)-5-fluoro-4-methyl-6-(trifluoromethyl)-5,6-dihydro-4H-1,3-oxazin-2-ylcarbamate B12d (54 mg, 132 μmol) was coupled with 5-cyanopicolinic acid according to the Ghosez's reagent-method to give after flash chromatography (SiO₂, gradient of EtOAc in heptane, 0 to 45% EtOAc) the title compound (55 mg, 102 μmol, 77.3% yield) as a white solid. MS (ESI): m/z=541.2 [M+H]⁺.

Example 1

N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide To a solution of tert-butyl (4S,6S)-4-(6-(5-cyanopicolinamido)-3-fluoropyridin-2-yl)-4-methyl-6-(trifluoromethyl)-5,6-dihydro-4H-1,3-oxazin-2-ylcarbamate (16 mg, 30.6 μmol, Eq: 1.00) in dichloromethane (0.5 ml) was added TFA (105 mg, 70.8 μl, 919 μmol, Eq: 30) at 10° C. The light yellow reaction solution was stirred at 23° C. for 3 hours. The solvent was evaporated, then basified with ice cold 1 N Na₂CO₃-sol., stirred for 15 min at 10° C., then extracted twice with ethyl acetate, washed the combined organic layers with brine, dried over Na₂SO₄, filtered and evaporated. The residue was purified by chromatography (silica gel, 5 g, 0-50% ethyl acetate in heptane, then 0-10% MeOH in ethyl acetate) to give N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide (9.5 mg, 22.5 μmol, 73.4% yield) as a white solid. MS (ISP): m/z=423.6 [(M+H)⁺].

Example 2

N-(6-((4S,6S)-2-Amino-4-methyl-6-(trifluoromethyl)-5,6-dihydro-4H-1,3-oxazin-4-yl)-5-fluoropyridin-2-yl)-3-chloro-5-cyanopicolinamide tert-Butyl (4S,6S)-4-(6-(3-chloro-5-cyanopicolinamido)-3-fluoropyridin-2-yl)-4-methyl-6-(trifluoromethyl)-5,6-dihydro-4H-1,3-oxazin-2-ylcarbamate B13a (18 mg) was deprotected to give the title compound (14 mg, 76%) as an off-white solid. MS (ESI): m/z=457.1, 459.1 [M+H]⁺.

Example 3

N-(6-((4S,6S)-2-Amino-4-methyl-6-(trifluoromethyl)-5,6-dihydro-4H-1,3-oxazin-4-yl)-5-fluoropyridin-2-yl)-3-chloro-5-(trifluoromethyl)picolinamide, salt with trifluoroacetic acid tert-Butyl (4S,6S)-4-(6-(3-chloro-5-(trifluoromethyl)picolinamido)-3-fluoropyridin-2-yl)-4-methyl-6-(trifluoromethyl)-5,6-dihydro-4H-1,3-oxazin-2-ylcarbamate B13a-2 (26 mg) was deprotected to give the title compound (27 mg, quant.) as a pale yellow solid. MS (ESI): m/z=500.3, 501.3 [M+H]⁺.

Example 4

N-(6-((4S,6S)-2-Amino-4-methyl-6-(trifluoromethyl)-5,6-dihydro-4H-1,3-oxazin-4-yl)-5-fluoropyridin-2-yl)-5-methoxypyrazine-2-carboxamide, salt with trifluoroacetic acid tert-Butyl (4S,6S)-4-(3-fluoro-6-(5-methoxypyrazine-2-carboxamido)pyridin-2-yl)-4-methyl-6-(trifluoromethyl)-5,6-dihydro-4H-1,3-oxazin-2-ylcarbamate B13a-3 (14 mg) was deprotected to give the title compound (14 mg, 80%) as an off-white solid. MS (ESI): m/z=429.6 [M+H]⁺.

Example 5

N-(6-((4S,6S)-2-Amino-4-methyl-6-(trifluoromethyl)-5,6-dihydro-4H-1,3-oxazin-4-yl)-5-fluoropyridin-2-yl)-5-cyano-3-methylpicolinamide, salt with trifluoroacetic acid tert-Butyl (4S,6S)-4-(6-(5-cyano-3-methylpicolinamido)-3-fluoropyridin-2-yl)-4-methyl-6-(trifluoromethyl)-5,6-dihydro-4H-1,3-oxazin-2-ylcarbamate B13a-4 (20 mg) was deprotected to give the title compound (21 mg, 78%) as an off-white solid. MS (ESI): m/z=437.5 [M+H]⁺.

Example 6

N-(6-((4S,6S)-2-Amino-4-methyl-6-(trifluoromethyl)-5,6-dihydro-4H-1,3-oxazin-4-yl)-5-fluoropyridin-2-yl)-5-methoxypicolinamide, salt with trifluoroacetic acid tert-Butyl (4S,6S)-4-(3-fluoro-6-(5-methoxypicolinamido)pyridin-2-yl)-4-methyl-6-(trifluoromethyl)-5,6-dihydro-4H-1,3-oxazin-2-ylcarbamate B13a-5 (16 mg) was deprotected to give the title compound (9 mg, 55%) as an off-white solid. MS (ESI): m/z=428.2 [M+H]⁺.

Example 7

N-(6-((4S,6S)-2-Amino-4-methyl-6-(trifluoromethyl)-5,6-dihydro-4H-1,3-oxazin-4-yl)-5-fluoropyridin-2-yl)-4-chloro-1-(difluoromethyl)-1H-pyrazole-3-carboxamide, salt with trifluoroacetic acid tert-Butyl (4S,6S)-4-(6-(4-chloro-1-(difluoromethyl)-1H-pyrazole-3-carboxamido)-3-fluoropyridin-2-yl)-4-methyl-6-(trifluoromethyl)-5,6-dihydro-4H-1,3-oxazin-2-ylcarbamate B13a-6 (23 mg) was deprotected to give the title compound (14 mg, 59%) as an off-white solid. MS (ESI): m/z=471.5, 473.5 [M+H]⁺.

Example 8

N-(6-((4S,6S)-2-Amino-4-methyl-6-(trifluoromethyl)-5,6-dihydro-4H-1,3-oxazin-4-yl)-5-fluoropyridin-2-yl)-5-(difluoromethyl)pyrazine-2-carboxamide, salt with trifluoroacetic acid tert-Butyl (4S,6S)-4-(6-(5-(difluoromethyl)pyrazine-2-carboxamido)-3-fluoropyridin-2-yl)-4-methyl-6-(trifluoromethyl)-5,6-dihydro-4H-1,3-oxazin-2-ylcarbamate B13a-7 (21 mg) was deprotected to give the title compound (18 mg, 84%) as an off-white solid. MS (ESI): m/z=449.2 [M+H]⁺.

Example 9

N-(6-((4S,6S)-2-Amino-4-methyl-6-(trifluoromethyl)-5,6-dihydro-4H-1,3-oxazin-4-yl)-5-fluoropyridin-2-yl)-3,5-dichloropicolinamide, salt with trifluoroacetic acid tert-Butyl (4S,6S)-4-(6-(3,5-dichloropicolinamido)-3-fluoropyridin-2-yl)-4-methyl-6-(trifluoromethyl)-5,6-dihydro-4H-1,3-oxazin-2-ylcarbamate B13a-8 (26 mg) was deprotected to give the title compound (21 mg, 90%) as a colorless solid. MS (ESI): m/z=466.4, 468.4, 470.4 [M+H]⁺.

Example 10

N-(6-((4S,6S)-2-Amino-4-methyl-6-(trifluoromethyl)-5,6-dihydro-4H-1,3-oxazin-4-yl)-5-fluoropyridin-2-yl)-5-(fluoromethoxy)picolinamide, salt with trifluoroacetic acid tert-Butyl (4S,6S)-4-(3-fluoro-6-(5-(fluoromethoxy)picolinamido)pyridin-2-yl)-4-methyl-6-(trifluoromethyl)-5,6-dihydro-4H-1,3-oxazin-2-ylcarbamate B13a-9 (16 mg) was deprotected to give the title compound (16 mg, 93%) as an off-white solid. MS (ESI): m/z=446.5 [M+H]⁺.

Example 11

N-(6-((4S,6S)-2-Amino-4-methyl-6-(trifluoromethyl)-5,6-dihydro-4H-1,3-oxazin-4-yl)-5-chloropyridin-2-yl)-5-cyanopicolinamide tert-Butyl (4S,6S)-4-(3-chloro-6-(5-cyanopicolinamido)pyridin-2-yl)-4-methyl-6-(trifluoromethyl)-5,6-dihydro-4H-1,3-oxazin-2-ylcarbamate B13b (4 mg) was deprotected with $CF_3COOH$ and evaporated. The residue was partitioned between saturated aqueous $Na_2CO_3$ and EtOAc, the organic layer was dried, evaporated and the residue purified by flash chromatography ($NH_2$-phase from Biotage, gradient of EtOAc in heptane, 0 to 50% EtOAc) to give the title compound (3 mg, 98%) as a white solid. MS (ESI): m/z=439.2, 441.2 [M+H]⁺.

Example 12

N-(6-((4R,5R,6S)-2-Amino-5-fluoro-4-methyl-6-(trifluoromethyl)-5,6-dihydro-4H-1,3-oxazin-4-yl)-5-fluoropyridin-2-yl)-5-cyanopicolinamide tert-Butyl (4R,5R,6S)-4-(6-(5-cyanopicolinamido)-3-fluoropyridin-2-yl)-5-fluoro-4-methyl-6-(trifluoromethyl)-5,6-dihydro-4H-1,3-oxazin-2-ylcarbamate B13c-1 (23 mg, 42.6 µmol) was deprotected and the crude material was purified by flash chromatography (silica gel, 10 g, 0% to 100% EtOAc in heptane) to give the title compound (12 mg, 27.3 µmol, 64.0% yield) as a white solid. MS (ESI): m/z=441.2 [M+H]⁺.

Example 13

N-(6-((4R,5R,6R)-2-Amino-5-fluoro-4-methyl-6-(trifluoromethyl)-5,6-dihydro-4H-1,3-oxazin-4-yl)-5-fluoropyridin-2-yl)-5-cyanopicolinamide tert-Butyl (4R,5R,6R)-4-(6-(5-cyanopicolinamido)-3-fluoropyridin-2-yl)-5-fluoro-4-methyl-6-(trifluoromethyl)-5,6-dihydro-4H-1,3-oxazin-2-ylcarbamate B13d-1 (55 mg, 102 µmol) was deprotected and the crude material was purified by flash chromatography (silica gel, 10 g, 0% to 100% EtOAc in heptane) to give the title compound (30 mg, 68.1 µmol, 66.9% yield) as a white foam. MS (ESI): m/z=441.2 [M+H]⁺.

The invention claimed is:
1. A compound of formula I,

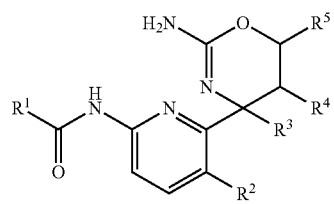

wherein
$R^1$ is selected from the group consisting of
  i) aryl,
  ii) aryl substituted by 1-4 substituents individually selected from amino, cyano, cyano-$C_{1-6}$-alkyl, halogen, halogen-$C_{1-6}$-alkoxy, halogen-$C_{1-4}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from amino, cyano, cyano-$C_{1-4}$-alkyl, halogen, halogen-$C_{1-6}$-alkoxy, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-4}$-alkoxy, $C_{2-6}$-alkynyl and $C_{1-4}$-alkyl;

R² is selected from the group consisting of
  i) hydrogen,
  ii) $C_{1-4}$-alkyl, and
  iii) halogen;
R³ is selected from the group consisting of
  i) $C_{1-6}$-alkyl, and
  ii) halogen-$C_{1-6}$-alkyl,
R⁴ is selected from the group consisting of
  i) halogen, and
  ii) hydrogen,
R⁵ is halogen-$C_{1-4}$-alkyl;
or a pharmaceutically acceptable salt thereof.

2. The compound of formula I, of formula Ia-1

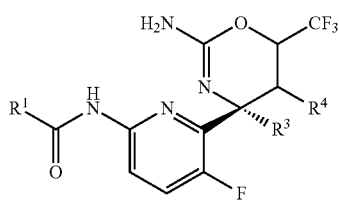

Ia-1 wherein
R¹ is selected from the group consisting of
  i) aryl,
  ii) aryl substituted by 1-2 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-4}$-alkyl,
  iii) heteroaryl, and
  iv) heteroaryl substituted by 1-2 substituents individually selected from amino, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl; and
R³ is selected from the group consisting of
  i) $C_{1-6}$-alkyl, and
  ii) halogen-$C_{1-6}$-alkyl,
R⁴ is selected from the group consisting of
  i) halogen, and
  ii) hydrogen,
or a pharmaceutically acceptable salt thereof.

3. The compound according to claim 1, wherein R¹ is heteroaryl substituted by 1-2 substituents individually selected from cyano, halogen, halogen-$C_{1-6}$-alkoxy, halogen-$C_{1-6}$-alkyl, $C_{1-6}$-alkoxy and $C_{1-6}$-alkyl.

4. The compound according to claim 1, wherein R¹ is heteroaryl substituted by 1-2 substituents individually selected from amino and cyano.

5. The compound according to claim 1, wherein R¹ is pyridinyl, 1H-pyrazolyl or pyrazinyl.

6. The compound according to claim 1, wherein R¹ is pyridinyl or pyrazinyl.

7. The compound according to claim 1, wherein R¹ is pyridinyl.

8. The compound according to claim 1, wherein R¹ is 3,5-dichloro-pyridinyl, 3-chloro-5-cyano-pyridinyl, 3-chloro-5-trifluoromethyl-pyridinyl, 4-chloro-1-(difluoromethyl)-1H-pyrazolyl, 5-(difluoromethyl)-pyrazinyl, 5-(fluoromethoxy)pyridinyl, 5-cyano-3-methyl-pyridinyl, 5-cyano-pyridinyl, 5-methoxy-pyrazinyl or 5-methoxy-pyridinyl.

9. The compound according to claim 1, wherein R¹ is 5-cyano-pyridine-2-yl.

10. The compound according to claim 1, wherein R² is halogen.

11. The compound according to claim 1, wherein R² is F.

12. The compound according to claim 1, wherein R³ is $C_{1-6}$-alkyl.

13. The compound according to claim 1, wherein R³ is methyl.

14. The compound according to claim 1, wherein R⁴ is halogen.

15. The compound according to claim 1, wherein R⁴ is fluoro.

16. The compound according to claim 1, wherein R⁴ is hydrogen.

17. The compound according to claim 1, wherein R⁵ is fluoro-$C_{1-6}$-alkyl.

18. The compound according to claim 1, wherein R⁵ is trifluoromethyl.

19. The compound according to claim 1 selected from the group consisting of:
  N-(6-((4R,5R,6R)-2-amino-5-fluoro-4-methyl-6-(trifluoromethyl)-5,6-dihydro-4H-1,3-oxazin-4-yl)-5-fluoropyridin-2-yl)-5-cyanopicolinamide,
  N-(6-((4R,5R,6S)-2-amino-5-fluoro-4-methyl-6-(trifluoromethyl)-5,6-dihydro-4H-1,3-oxazin-4-yl)-5-fluoropyridin-2-yl)-5-cyanopicolinamide,
  N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide,
  N-(6-((4S,6S)-2-amino-4-methyl-6-(trifluoromethyl)-5,6-dihydro-4H-1,3-oxazin-4-yl)-5-fluoropyridin-2-yl)-3-chloro-5-cyanopicolinamide,
  N-(6-((4S,6S)-2-amino-4-methyl-6-(trifluoromethyl)-5,6-dihydro-4H-1,3-oxazin-4-yl)-5-fluoropyridin-2-yl)-3-chloro-5-(trifluoromethyl)picolinamide 2,2,2-trifluoroacetate,
  N-(6-((4S,6S)-2-amino-4-methyl-6-(trifluoromethyl)-5,6-dihydro-4H-1,3-oxazin-4-yl)-5-fluoropyridin-2-yl)-5-methoxypyrazine-2-carboxamide 2,2,2-trifluoroacetate,
  N-(6-((4S,6S)-2-amino-4-methyl-6-(trifluoromethyl)-5,6-dihydro-4H-1,3-oxazin-4-yl)-5-fluoropyridin-2-yl)-5-cyano-3-methylpicolinamide 2,2,2-trifluoroacetate,
  N-(6-((4S,6S)-2-amino-4-methyl-6-(trifluoromethyl)-5,6-dihydro-4H-1,3-oxazin-4-yl)-5-fluoropyridin-2-yl)-5-methoxypicolinamide 2,2,2-trifluoroacetate,
  N-(6-((4S,6S)-2-amino-4-methyl-6-(trifluoromethyl)-5,6-dihydro-4H-1,3-oxazin-4-yl)-5-fluoropyridin-2-yl)-4-chloro-1-(difluoromethyl)-1H-pyrazole-3-carboxamide 2,2,2-trifluoroacetate,
  N-(6-(4S,6S)-2-amino-4-methyl-6-(trifluoromethyl)-5,6-dihydro-4H-1,3-oxazin-4-yl)-5-fluoropyridin-2-yl)-5-(difluoromethyl)pyrazine-2-carboxamide 2,2,2-trifluoroacetate,
  N-(6-((4S,6S)-2-amino-4-methyl-6-(trifluoromethyl)-5,6-dihydro-4H-1,3-oxazin-4-yl)-5-fluoropyridin-2-yl)-3,5-dichloropicolinamide 2,2,2-trifluoroacetate,
  N-(6 ((4S,6S)-2-amino-4-methyl-6-(trifluoromethyl)-5,6-dihydro-4H-1,3-oxazin-4-yl)-5-fluoropyridin-2-yl)-5-(fluoromethoxy)picolinamide 2,2,2-trifluoroacetate, and
  N-(6-((4S,6S)-2-amino-4-methyl-6-(trifluoromethyl)-5,6-dihydro-4H-1,3-oxazin-4-yl)-5-chloropyridin-2-yl)-5-cyanopicolinamide,
  or a pharmaceutically acceptable salt thereof.

20. The compound according to claim 1, wherein said compound is N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide or a pharmaceutically acceptable salt thereof.

21. A process for preparing a compound according to claim 1, comprising the step of reacting a compound of formula XI' with a compound of formula XII'

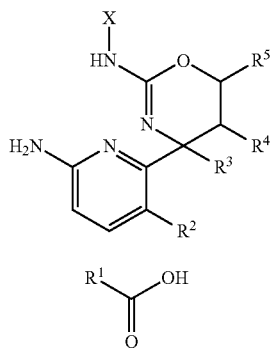
XI'

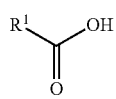
XII' to form a compound of formula I, wherein $R^1$, $R^2$, $R^3$, $R^4$ and $R^5$ are as defined in claim 1 and X is an amino protecting group.

22. A pharmaceutical composition, comprising a therapeutically effective amount of a compound according to claim 1 and a pharmaceutically acceptable carrier and/or a pharmaceutically acceptable auxiliary substance.

23. A method for treating a disease or disorder characterized by elevated β-amyloid levels and/or β-amyloid oligomers and/or β-amyloid plaques and further deposits or Alzheimer's disease, comprising the step of administering a therapeutically effective amount of a compound according to claim 1 to a human being or animal in need thereof.

24. A method for treating Alzheimer's disease, comprising the step of administering a therapeutically effective amount of a compound according to claim 1 to a human being or animal in need thereof.

* * * * *

UNITED STATES PATENT AND TRADEMARK OFFICE
CERTIFICATE OF CORRECTION

PATENT NO. : 11,447,478 B2
APPLICATION NO. : 14/783478
DATED : September 20, 2022
INVENTOR(S) : Hans Hilpert et al.

It is certified that error appears in the above-identified patent and that said Letters Patent is hereby corrected as shown below:

In the Claims

At Column 70, Line 59, "halogen-C1-4-alkyl" should be printed as "halogen-C1-6-alkyl."

At Column 70, Line 64, "cyano-C1-4-alkyl" should be printed as "cyano-C1-6-alkyl."

At Column 70, Line 67, "C1-4-alkoxy, C2-6-alkynyl and C1-4-alkyl" should be printed as "C1-6-alkoxy, C2-6-alkynyl and C1-6-alkyl."

At Column 71, Line 3, "C1-4-alkyl" should be printed as "C1-6-alkyl."

At Column 71, Line 11, "R5 is halogen-C1-4-alkyl" should be printed as "R5 is halogen-C1-6-alkyl."

At Column 71, Line 33, "alkoxy, C2-6-alkynyl and C1-4-alkyl" should be printed as "alkoxy, C2-6-alkynyl and C1-6-alkyl."

Signed and Sealed this
Fifteenth Day of November, 2022

Katherine Kelly Vidal
*Director of the United States Patent and Trademark Office*